United States Patent [19]

Riniker et al.

[11] Patent Number: 4,595,677

[45] Date of Patent: Jun. 17, 1986

[54] SUBSTITUTED TETRAPEPTIDES

[75] Inventors: Bernhard Riniker, Frenkendorf; Peter Bühlmayer, Arlesheim; Walter Fuhrer, Frenkendorf, all of Switzerland

[73] Assignee: Ciba-Geigy Corporation, Ardsley, N.Y.

[21] Appl. No.: 554,735

[22] Filed: Nov. 23, 1983

[30] Foreign Application Priority Data

Dec. 3, 1982 [CH] Switzerland .................. 7047/82
Jul. 1, 1983 [CH] Switzerland .................. 3635/83

[51] Int. Cl.$^4$ .................. C07K 7/02; A61K 37/02
[52] U.S. Cl. .................. 514/17; 530/330; 530/331
[58] Field of Search .................. 260/112.5 R

[56] References Cited

U.S. PATENT DOCUMENTS

| | | | |
|---|---|---|---|
| 4,218,474 | 8/1980 | Barnish et al. | 424/177 |
| 4,384,994 | 5/1983 | Veber et al. | 260/112.5 R |
| 4,424,207 | 1/1984 | Szelke et al. | 260/112.5 R |
| 4,470,971 | 9/1984 | Boger et al. | 260/112.5 R |
| 4,478,826 | 10/1984 | Veber et al. | 260/112.5 K |
| 4,479,941 | 10/1984 | Veber et al. | 260/112.5 R |
| 4,481,192 | 11/1984 | Sanofi | 260/112.5 R |
| 4,485,099 | 11/1984 | Boger et al. | 260/112.5 R |

FOREIGN PATENT DOCUMENTS 0077028 4/1983 European Pat. Off.
0081783 6/1983 European Pat. Off.

OTHER PUBLICATIONS

*Chemical Abstracts*, 98, 249(1983), Abst. No. 139574g.
Parsons, *Peptide Hormones*, U. Park Press, 1-7, (1976).
Szelke et al., *Nature*, vol. 299, pp. 555-557 (1982).

*Primary Examiner*—Delbert R. Phillips
*Assistant Examiner*—F. T. Moezie
*Attorney, Agent, or Firm*—Michael W. Glynn; Irving M. Fishman

[57] ABSTRACT

Tetrapeptides of the formula I,

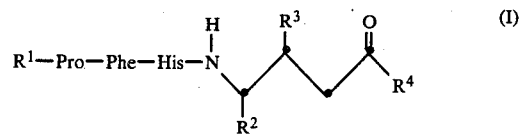

in which $R^1$ represents hydrogen or acyl, $R^2$ represents alkyl or aralkyl, $R^3$ represents free or functionally modified hydroxy, $R^4$ represents free or substituted amino or free or etherified hydroxy, and -Pro-, -Phe- and -His- respectively represent the bivalent radicals of the amino acids proline, phenylalanine and histidine or the (D)-isomers thereof, salts of such compounds having salt-forming groups, and processes for their manufacture.

The compounds inhibit the action of the enzyme renin and can be used as antihypertensives and for the treatment of cardiac insufficiency.

17 Claims, No Drawings

SUBSTITUTED TETRAPEPTIDES

The invention relates to substituted tetrapeptides of the formula I

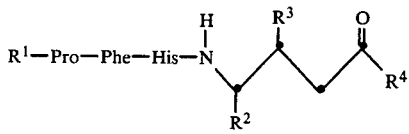

in which
R¹ represents hydrogen or acyl,
R² represents alkyl or aralkyl,
R³ represents free or functionally modified hydroxy,
R⁴ represents free or substituted amino or free or etherified hydroxy,
and
-Pro-, -Phe- and -His- respectively represent the bivalent radicals of the amino acids proline, phenylalanine and histidine or the (D)-isomers thereof,
salts of such compounds having salt-forming groups, processes for the manufacture of these compounds, pharmaceutical preparations containing these compounds, their use for the manufacture of pharmaceutical preparations or as pharmacologically active compounds, and novel intermediates for the manufacture of compounds of the formula I.

Acyl as the radical R¹ has especially up to 80 carbon atoms and is principally aliphatic, aromatic, aromatic-aliphatic, heterocyclic or heterocyclic-aliphatic acyl. Acyl as the radical R¹ is especially the acyl radical of a naturally occurring (L)-amino acid, such as histidine, or the (D)-isomer thereof, the acyl radical of a dipeptide consisting of two naturally occurring (L)-amino acids or the (D)-isomers thereof, the acyl radical of an oligopeptide having from 3 to 6 naturally occurring amino acids and at most 60 carbon atoms, any free functional groups in these amino acid radicals optionally being in protected from, or another aliphatic, aromatic or aromatic-aliphatic acyl radical having up to 18 carbon atoms. Preferably, R¹ represents the dipeptidyl radical H-Arg-Arg-, H-Pro-His- or H-Ile-His- in which each of the two amino acids, independently of the other, can have the (D)- or (L)-configuration, but have especially the (L)-configuration. An oligopeptide radical R¹ preferably has a histidyl radical at the carboxyl end which in turn may be bonded preferably to a prolyl or isoleucyl radical. The further amino acid sequence is essentially optional. As examples of an oligopeptide radical R¹ there may be mentioned, therefore, the radical H-Asp-Arg-Val-Tyr-Ile (or Pro)-His- or parts thereof which are characterised by the absence of from 1 to 3 amino acids from the amino end.

Alkyl as the radical R² has especially from 1 to 18 carbon atoms and is more especially lower alkyl, the prefix "lower" denoting here and hereinafter a radical having from and including 1 up to and including 7, principally from and including 1 up to and including 4, carbon atoms. Preferably an alkyl radical R² is branched lower alkyl, above all 2-methylpropyl. Aralkyl as the radical R² has primarily not more than 18 carbon atoms and is especially unsubstituted phenyl-lower alkyl or phenyl-lower alkyl that is substituted in the phenyl radical, and is more especially benzyl. As aryl substituents there may be mentioned especially lower alkyl, free or functionally modified hydroxy and free or esterified carboxy. An aryl radical may carry one or more, for example two or three and, as a rule, not more than five, identical or different substituents.

Functionally modified hydroxy as an aryl substituent is esterified or etherified hydroxy. Esterified hydroxy is hydroxy esterified by an organic or inorganic acid, for example acyloxy, sulphonyloxy or halogen. Acyloxy is especially lower aliphatic acyloxy, cycloaliphatic acyloxy having from 3 to 6, primarily 5 or 6, ring members and at most 12 carbon atoms, monocyclic aroyloxy having at most 12 carbon atoms or aromatic-aliphatic acyloxy having at most 12 carbon atoms. Etherified hydroxy as an aryl substituent is especially hydroxy nominally etherified by an aliphatic, aromatic or aromatic-aliphatic alcohol having at most 12 carbon atoms, especially lower alkoxy.

Esterified carboxy as an aryl substituent is especially hydroxy nominally esterified by an aliphatic, aromatic or aromatic-aliphatic alcohol having at most 12 carbon atoms, especially lower alkoxycarbonyl.

Functionally modified hydroxy as the radical R³ is hydroxy esterified by an organic carboxylic acid, but may also be etherified hydroxy. Suitable esterifying or etherifying radicals are principally radicals that can be removed in the human or animal organism and which, after removal, form cleavage products that are pharmacologically harmless in the concentration involved. Esterified hydroxy as the radical R³ is especially acyloxy having up to 18 carbon atoms and more especially lower aliphatic acyloxy, cycloaliphatic acyloxy having from 3 to 6, principally 5 or 6, ring members and at most 12 carbon atoms, or monocyclic aroyloxy or aromatic-aliphatic acyloxy each of which has at most 12 carbon atoms.

Etherified hydroxy as the radical R³ is especially hydroxy nominally etherified by an aliphatic, aromatic or aromatic-aliphatic alcohol having at most 12 carbon atoms.

Substituted amino as the radical R⁴ is, for example, amino that is mono- or di-substituted by lower alkyl and/or aryl-lower alkyl or is the amidically bonded radical of a naturally occurring amino acid or the (D)-isomer thereof or of a peptide having from 2 to 6 amino acids and at most 60 carbon atoms which consists of naturally occurring amino acids or the (D)-isomers thereof, any free functional groups in these amino acid or peptide radicals being optionally in protected form, and is above all the radical of a peptide having from 2 to 6, preferably 2 or 3, amino acids that has at the N-terminal end one of the following amino acid sequences: -Val-Tyr-Lys-, -Ile-His-Lys-, -Ile-His-Ser-, -Val-Tyr-Ser- or -Ala-Sta-.

Etherified hydroxy as the radical R⁴ is hydroxy nominally etherified by an aliphatic, aromatic or aromatic-aliphatic alcohol having at most 12 carbon atoms, especially lower alkoxy, or especially the radical of a hydroxycarboxylic acid which in turn is optionally amidated with an amino acid or a dipeptide.

The compounds of the formula I can have at C-R² and C-R³ independently of each other the (R)- or the (S)-configuration, but preferably have the (S,S)-configuration.

Within the scope of the present description the general definitions used hereinbefore and hereinafter have preferably the following meanings:

Lower alkyl is above all methyl, ethyl, n-propyl, isopropyl, n-butyl or isobutyl, but may also be, for example, sec.-butyl or tert.-butyl, and also n-pentyl, neopentyl, n-hexyl or n-heptyl.

Halogen is especially chlorine or bromine, but may also be fluorine or iodine.

Naturally occurring amino acids are especially those 20 amino acids which regularly occur in proteins, namely glycine (H-Gly-OH), alanine (H-Ala-OH), proline (H-Pro-OH), serine (H-Ser-OH), cysteine (H-Cys-OH), tyrosine (H-Tyr-OH), asparagine (H-Asn-OH), glutamine (H-Gln-OH), aspartic acid (H-Asp-OH), glutamic acid (H-Glu-OH), arginine (H-Arg-OH), histidine (H-His-OH), and those 8 amino acids which are essential for humans, namely valine (H-Val-OH), leucine (H-Leu-OH), isoleucine (H-Ile-HO), lysine (H-Lys-OH), phenylalanine (H-Phe-OH) tryptophan (H-Trp-OH), methionine (H-Met-OH) and threonine (H-Thr-OH). Of the other naturally occurring amino acids there are to be mentioned here, for example, hydroxyproline, sarcosine (H-Sar-OH), β-aminocarboxylic acids, for example β-alanine (H-β-Ala-OH), γ-aminocarboxylic acids, for example γ-aminobutyric acid, α,γ-diaminocarboxylic acids, for example ornithine, and above all 4-amino-3-hydroxy-6-methyl-heptanecarboxylic acid (statin, abbreviated here to "H-Sta-OH"). Unless stated otherwise, the abbreviations given denote the amino acids in their natural configuration.

A hydroxycarboxylic acid is especially a monohydroxymonocarboxylic acid, especially an α-hydroxymonocarboxylic acid, for example glycolic acid or lactic acid (abbreviated to: H-Lac-OH).

Aromatic radicals are especially optionally substituted phenyl radicals. Substituents of aromatic radicals are especially lower alkyl, free or functionally modified hydroxy and/or free or esterified carboxy.

Aliphatic radicals are especially acyclic, unsubstituted or substituted hydrocarbon radicals without cyclic substituents, which are saturated or unsaturated by one or two double bonds and in which the free valence must extend from a carbon atom that is not substituted by oxo, and are especially unsubstituted or substituted alkyl radicals, for example lower alkyl radicals. Preferred substituents of such aliphatic radicals are free or functionally modified hydroxy or mercapto, free or esterified carboxy and/or free or substituted amino.

Heterocyclic radicals are principally mono- or bicyclic, primarily having from 3 to 7 ring members per closed ring, and have as hetero atoms especially oxygen, sulphur and/or nitrogen and may contain up to 4 hetero atoms. In the case of $R^1$ they have primarily 5 or 6, and above all 5, ring members in a monocyclic heterocyclic ring that contains as hetero atoms exclusively one or two nitrogen atoms and may be benzoannellated.

The compounds of the formula I may be in the form of pure, optically active isomers or in the form of isomeric mixtures. Salt-forming groups in a compound of the formula I are either acidic groups, such as especially carboxy groups or also sulphonic acid groups, or basic groups, such as especially those which contain basic nitrogen atoms, for example amino groups. Salts of compounds of the formula I having salt-forming groups are especially pharmaceutically acceptable, non-toxic salts, such as salts of acidic compounds of the formula I with bases, especially suitable alkali metal salts, such as sodium or potassium salts, or alkaline earth metal salts, for example magnesium or calcium salts, and also zinc salts or ammonium salts, including those with organic amines, such as mono-, di- or tri-alkylamines optionally substituted by hydroxy, for example diethylamine, di(2-hydroxyethyl)-amine, triethylamine, N,N-dimethyl-N-(2-hydroxyethyl)-amine, tri-(2-hydroxyethyl)-amine or N-methyl-D-glucamine, or salts of basic compounds of the formula I with acids, such as salts with inorganic acids, for example hydrochloric acid, sulphuric acid or phosphoric acid, or salts with organic carboxylic, sulphonic or sulpho acids, for example acetic acid, propionic acid, glycolic acid, succinic acid, maleic acid, hydroxymaleic acid, methylmaleic acid, fumaric acid, malic acid, tartaric acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, also amino acids, such as, for example, those mentioned above, and also methanesulphonic acid, ethanesulphonic acid, 2-hydroxyethanesulphonic acid, ethane-1,2-disulphonic acid, benzenesulphonic acid, 4-methylbenzenesulphonic acid or naphthalene-2-sulphonic acid, or with other acidic organic compounds, such as ascorbic acid. Compounds of the formula I having acidic or basic groups may also form internal salts.

For the purposes of isolation or purification, pharmaceutically unsuitable salts also can be used. Only pharmaceutically acceptable, non-toxic salts are used therapeutically and these are therefore preferred.

The compounds of the present invention have enzyme-inhibiting actions; in particular they inhibit the action of the natural enzyme renin. The latter passes from the kidneys into the blood and there brings about the cleavage of a blood glycoprotein (angiotensinogen) with the decapeptide angiotensin I being formed, which is then cleaved in the lungs, the kidneys and other organs to form the octapeptide angiotensin II. The latter raises the blood pressure both directly through arterial constriction and indirectly through releasing from the adrenal gland the hormone aldosterone which retains sodium, which involves an increase in the extracellular fluid volume. This increase is to be attributed to the action of angiotensin II itself or of the heptapeptide angiotensin III formed therefrom as a cleavage product. Inhibitors of the enzymatic activity of renin bring about an inhibition of the formation of angiotensin I. As a consequence of this less angiotensin II is produced and the reduced concentration of this active peptide hormone is ultimately responsible for the pharmacological action of renin-inhibitors.

The action of renin-inhibitors is detected, inter alia, by means of in vitro methods, the reduction in the formation of angiotensin I being measured in various systems (human plasma, purified human renin together with synthetic or natural renin substrate). The following in vitro test inter alia is used: An extract of human renin from the kidney (0.5 m GU [milli gold leaf units]/ml) is incubated for one hour at 37° C. and pH 7.2 in 1 molar aqueous 2-N-(trishydroxymethyl-methyl)-amino-ethanesulphonic acid-buffer solution containing 23 ug/ml synthetic tetradecapeptide substrate (H-Asp-Arg-Val-Tyr-Ile-His-Pro-Phe-His-Leu-Leu-Val-Tyr-Ser-OH). The amount of angiotensin I formed is determined by a radioimmunoassay. The inhibiting substances are each added to the incubation mixture in different concentrations. $IC_{50}$ denotes that concentration of the particular inhibiting substance which reduces the formation of angiotensin I by 50%. In the in vitro systems the compounds of the present invention exhibit inhibiting actions at minimum dosages of from approximately $10^{-7}$ to approximatel $10^{-10}$ mol/liter.

In animals depleted of salt the renin-inhibitors bring about a fall in blood pressure. Since human renin differs from that of other species, primates (marmosets, *Callithrix jacchus*) are used for testing inhibitors of human renin. The following in vivo test inter alia is used:

The test compounds are evaluated in conscious normotensive marmosets of both sexes having a body weight of approximately 300 g. Blood pressure and heart rate are measured by means of a catheter in the femoral artery. The test substances are injected via a catheter into the lateral caudal vein. The endogenous release of renin is triggered by intravenous injection of Furosemid (5 mg/kg). 30 minutes after the injection of Furosemid the test substances are administered either by a single injection or by continuous infusion and their effect on the blood pressure and the heart rate is evaluated. The compounds of the present invention are effective in the in vivo systems at dosages of from approximately 0.1 to approximately 1.0 mg/kg i.v.

The compounds of the present invention can be used as antihypertensives, also for the treatment of cardiac insufficiency and also for the diagnosis of the causes of high blood pressure or of an unduly high aldosterone level.

Pharmaceutically unacceptable compounds of the formula I in which functional groups, such as carboxy, amino, hydroxy or mercapto groups, are in protected form are especially intermediates for the manufacture of pharmaceutically acceptable compounds of the formula I and the invention relates also to these.

Compounds of the formula I in which functional groups, especially carboxy and amino groups, and preferably all carboxy and amino groups, are protected by pharmaceutically acceptable protecting groups, for example carboxy groups in the form of lower alkyl esters, for example methyl esters, and amino groups in the form of tert.-butoxycarbonyl- or benzyloxycarbonylamino, can be used pharmaceutically as compounds having a prolonged period of action as compared with the corresponding unprotected compounds, and the invention accordingly relates preferably to these protected compounds.

Protecting groups and the methods by which they are introduced and removed are described, for example, in "Protective Groups in Organic Chemistry", Plenum Press, London, New York 1973, and in "Methoden der organischen Chemie", Houben-Weyl, 4th edition, vol. 15/1, Georg-Thieme-Verlag, Stuttgart 1974. A characteristic feature of protecting groups is that they can readily be removed, i.e. without undesired side reaction occurring, for example by solvolysis, reduction, photolysis or also under physiological conditions.

Carboxy groups are usually protected in esterified form, such ester groupings being readily cleavable under mild conditions. Carboxy groups protected in this manner contain as esterifying groups especially lower alkyl groups branched in the 1-position or suitably substituted in the 1- or 2-position. Preferred carboxy groups that are in esterified form are, inter alia, tert.-lower alkoxycarbonyl, for example tert.-butoxycarbonyl, arylmethoxycarbonyl having one or two aryl radicals, these being phenyl radicals that are optionally mono- or poly-substituted, for example by lower alkyl, such as tert.-lower alkyl, for example tert.-butyl, lower alkoxy, such as methoxy, hydroxy, halogen, for example chlorine, and/or by nitro, such as benzyloxycarbonyl that is optionally substituted, for example as mentioned above, for example 4-methoxybenzyloxycarbonyl or 4-nitrobenzyloxycarbonyl, or diphenylmethoxycarbonyl that is optionally substituted, for example as mentioned above, for example diphenylmethoxycarbonyl or di-(4-methoxyphenyl)-methoxycarbonyl, 1-lower alkoxy-lower alkoxycarbonyl, such as methoxymethoxycarbonyl, 1-methoxyethoxycarbonyl or 1-ethoxymethoxycarbonyl, 1-lower alkylthio-lower alkoxycarbonyl, such as 1-methylthiomethoxycarbonyl or 1-ethylthioethoxycarbonyl, aroylmethoxycarbonyl in which the aroyl group represents benzoyl that is optionally substituted, for example by halogen, such as bromine, for example phenacyloxycarbonyl, 2-halo-lower alkoxycarbonyl, for example 2,2,2-trichloroethoxycarbonyl, 2-bromoethoxycarbonyl or 2-iodoethoxycarbonyl, or 2-(tri-substituted silyl)-ethoxycarbonyl in which each of the substituents, independently of the others, represents an aliphatic, araliphatic, cycloaliphatic or aromatic hydrocarbon radical that is optionally substituted, for example by lower alkyl, lower alkoxy, aryl, halogen and/or by nitro, such as corresponding, optionally substituted lower alkyl, phenyl-lower alkyl, cycloalkyl or phenyl, for example 2-tri-lower alkylsilylethoxycarbonyl, such as 2-trimethylsilylethoxycarbonyl or 2-(di-n-butyl-methyl-silyl)-ethoxycarbonyl, or 2-triarylsilylethoxycarbonyl, such as 2-triphenylsilylethoxycarbonyl.

The organic silyl or stannyl radicals mentioned hereinbefore and hereinafter contain preferably lower alkyl, especially methyl, as substituent of the silicon or tin atoms. Correponding silyl or stannyl groups are especially tri-lower alkylsilyl, especially trimethylsilyl, also dimethyl-tert.-butyl-silyl, or correspondingly substituted stannyl, for example tri-n-butylstannyl.

Preferred protected carboxy groups are tert.-lower alkoxycarbonyl, such as tert.-butyoxycarbonyl, and especially benzyloxycarbonyl that is optionally substituted, for example as mentioned above, for example 4-nitrobenzyloxycarbonyl, or diphenylmethoxycarbonyl, and above all 2-(trimethylsilyl)-ethoxycarbonyl.

A protected amino group can be, for example, in the form of a readily cleavable acylamino, arylmethylamino, etherified mercaptoamino, 2-acyl-lower alk-1-en-1-ylamino, silylamino or stannylamino group, or in the form of an azido group.

In a corresponding acylamino group, acyl is, for example, the acyl radical of an organic carboxylic acid having, for example, up to 18 carbon atoms, especially of an alkanecarboxylic acid that is optionally substituted, for example by halogen or aryl, or of benzoic acid that is optionally substituted, for example by halogen, lower alkoxy or nitro, or of a carbonic acid semiester. Such acyl groups are, for example, lower alkanoyl, such as formyl, acetyl or propionyl, halo-lower alkanoyl, such as 2-haloacetyl, especially 2-chloro-, 2-bromo-, 2-iodo-, 2,2,2-trifluoro- or 2,2,2-trichloro-acetyl, benzoyl that is optionally substituted, for example by halogen, lower alkoxy or nitro, for example benzoyl, 4-chlorobenzoyl, 4-methoxybenzoyl or 4-nitrobenzoyl, or lower alkoxycarbonyl that is branched in the 1-position of the lower alkyl radical or suitably substituted in the 1- or 2-position, especially tert.-lower alkoxycarbonyl, for example tert.-butoxycarbonyl, arylmethoxycarbonyl having one or two aryl radicals in which aryl is preferably phenyl that is optionally mono- or polysubstituted, for example by lower alkyl, especially tert.-lower alkyl, such as tert.-butyl, lower alkoxy, such as methoxy, hydroxy, halogen, for example chlorine, and/or by nitro, such as optionally substituted benzyloxycarbonyl, for example 4-nitrobenzyloxycarbonyl, or substituted diphenylmethoxycarbonyl, for example benzhydryloxycarbonyl or di-(4-methoxyphenyl)-methoxycarbonyl, aroylmethoxycarbonyl in which the aroyl group is preferably benzoyl that is optionally substituted, for example by halogen, such as bromine, for example phenacyloxycarbonyl, 2-halo-lower alkoxycarbonyl, for example 2,2,2-trichloroethoxycarbonyl, 2-bromoethoxycarbonyl or 2-iodoethoxycarbonyl, or 2-(tri-substituted silyl)-ethoxycarbonyl in which each of the substituents, independently of the others, represents an aliphatic, araliphatic, cycloaliphatic or aromatic hydrocarbon radical having, for example, up to 15 carbon atoms that is optionally substituted, for example by lower alkyl, lower alkoxy, aryl, halogen or by nitro, such as corresponding, optionally substituted lower alkyl, phenyl-lower alkyl, cycloalkyl or phenyl, for example 2-tri-lower alkylsilylethoxycarbonyl or 2-(di-n-butyl-methyl-silyl)-ethoxycarbonyl, or 2-triarylsilylethoxycarbonyl, such as 2-triphenylsilylethoxycarbonyl.

Further acyl radicals coming into consideration as amino-protecting groups are also corresponding radicals of organic phosphoric, phosphonic or phosphinic acids, such as di-lower alkylphosphoryl, for example dimethylphosphoryl, diethylphosphoryl, di-n-propylphosphoryl or diisopropylphosphoryl, dicycloalkylphosphoryl, for example dicyclohexylphosphoryl, optionally substituted diphenylphosphoryl, for example diphenylphosphoryl, di(phenyl-lower alkyl)-phosphoryl that is optionally substituted, for example by nitro, for example dibenzylphosphoryl or di-(4-nitrobenzyl)-phosphoryl, optionally substituted phenoxy-phenyl-phosphonyl, for example phenoxy-phenyl-phosphonyl, di-lower alkylphosphinyl, for example diethylphosphinyl, or optionally substituted diphenylphosphinyl, for example diphenylphosphinyl.

In an arylmethylamino group that is mono-, di- or especially tri-arylmethylamino, the aryl radicals are especially optionally substituted phenyl radicals. Such groups are, for example, benzyl-, diphenylmethyl- and especially trityl-amino.

An etherified mercapto group in an amino group protected by such a radical is especially arylthio or aryl-lower alkylthio in which aryl is especially phenyl that is optionally substituted, for example by lower alkyl, such as methyl or tert.-butyl, lower alkoxy, such as methoxy, halogen, such as chlorine, and/or nitro. A corresponding amino-protecting group is, for example, 4-nitrophenylthio.

In a 2-acyl-lower alk-1-en-1-yl group that may be used as an amino-protecting group, acyl is, for example, the corresponding radical of a lower alkanecarboxylic acid, or of a benzoic acid that is optionally substituted, for example by lower alkyl, such as methyl or tert.-butyl, lower alkoxy, such as methoxy, halogen, such as chlorine, and/or nitro, or especially of a carbonic acid semiester, such as a carbonic acid lower alkyl semiester. Corresponding protecting groups are especially 1-lower alkanoylprop-1,-en-2-yl, for example 1-acetylprop-1-en-2-yl, or 1-lower alkoxycarbonylprop-1-en-2-yl, for example 1-ethoxycarbonylprop-1-en-2-yl.

An amino group may also be protected in protonated form; as corresponding anions there come into consideration especially those of strong inorganic acids, such as hydrohalic acids, for example the chlorine or bromine anion, or of organic sulphonic acids, such as p-toluenesulphonic acid.

Preferred amino-protecting groups are acyl radicals of carbonic acid semiesters, especially tert.-butoxycarbonyl, or benzyloxycarbonyl that is optionally substituted, for example as indicated, for example 4-nitrobenzyloxycarbonyl, or diphenylmethoxycarbonyl, or 2-halo-lower alkoxycarbonyl, such as 2,2,2-trichloroethoxycarbonyl, or trityl or formyl.

Hydroxy-protecting groups are, for example, acyl radicals, such as lower alkanoyl optionally substituted, for example, by halogen, such as 2,2-dichloroacetyl, or acyl radicals of carbonic acid semiesters, especially tert.-butoxycarbonyl, optionally substituted benzyloxycarbonyl, for example 4-nitrobenzyloxycarbonyl, or diphenylmethoxycarbonyl, or 2-halo-lower alkoxycarbonyl, such as 2,2,2-trichloroethoxycarbonyl, or trityl or formyl, or organic silyl or stannyl radicals, also readily removable etherifying groups, such as tert.-lower alkyl, for example tert.-butyl, 2-oxa- or 2-thia-aliphatic or -cycloaliphatic hydrocarbon radicals, especially 1-lower alkoxy-lower alkyl or 1-lower alkylthio-lower alkyl, for example methoxymethyl, 1-methoxyethyl, 1-ethoxyethyl, 1-methylthiomethyl, 1-methylthioethyl or 1-ethylthioethyl, or 2-oxa- or 2-thia-cycloalkyl having 5 or 6 ring atoms, for example 2-tetrahydrofuryl or 2-tetrahydropyranyl or corresponding thia analogues, and also optionally substituted 1-phenyl-lower alkyl, such as optionally substituted benzyl or diphenylmethyl, suitable substituents of the phenyl radicals being, for example, halogen, such as chlorine, lower alkoxy, such as methoxy, and/or nitro.

A mercapto group, such as, for example, in cysteine, can be protected especially by S-alkylation with optionally substituted alkyl radicals, by thioacetal formation, S-acylation or by establishing asymmetric disulphide groupings. Preferred mercapto-protecting groups are, for example, benzyl optionally substituted in the phenyl radical, for example by methoxy or nitro, such as 4-methoxybenzyl, diphenylmethyl optionally substituted in the phenyl moiety, for example by methoxy, such as 4,4'-dimethoxydiphenylmethyl, triphenylmethyl, trimethylsilyl, benzylthiomethyl, tetrahydropyranyl, acylaminomethyl, benzoyl, benzyloxycarbonyl or aminocarbonyl, such as ethylaminocarbonyl.

The protection of amide groups is only seldom necessary. Preferred amiqe-protecting groups are, for example, 4-, 2,4-di- or 2,4,6-tri-methoxybenzyl, or diphenylmethyl optionally substituted in the phenyl radical by methyl or methoxy, for example 4,4'-dimethoxydiphenylmethyl, these groups being bonded to the nitrogen atom.

The invention relates especially to compounds of the formula I in which $R^1$ represents hydrogen, an aliphatic, aromatic or aromatic-aliphatic acyl radical having up to 18 carbon atoms, a heterocyclic or heterocyclic-aliphatic acyl radical each of which has 5 or 6 ring members and one or two nitrogen atoms in the optionally benzoannellated heterocyclic ring and a total of not more than 18 carbon atoms, or the acyl radical of an oligopeptide having more than 18 and at most 60 carbon atoms which consists of at most 6 naturally occurring amino acids and/or the (D)-isomers thereof, any free functional groups in such amino acids optionally being in protected form, $R^2$ represents alkyl or aralkyl each of which has not more than 18 carbon atoms, $R^3$ represents free or esterified hydroxy having at most 18 carbon atoms, and $R^4$ represents free amino or amino substituted by aryl-lower alkyl having at most 18 carbon atoms or by lower alkyl, the N-terminal radical of a naturally occurring amino acid or the (D)-isomer thereof, or of a peptide consisting of from 2 to 6 naturally occurring amino acids and/or the (D)-isomers thereof, any free functional groups in such amino acids optionally being in protected form, or free or etherified hydroxy having at most 12 carbon atoms, and salts of such compounds having salt-forming groups.

The invention relates chiefly to compounds of the formula I in which $R^1$ represents hydrogen, the radical of a naturally occurring amino acid or the (D)-isomer thereof, or the radical of a peptide consisting of at most 6 naturally occurring amino acids and/or the (D)-isomers thereof, any free functional groups in these radicals optionally being in protected form, $R^2$ represents lower alkyl or phenyl-lower alkyl, $R^3$ represents free hydroxy, and $R^4$ represents free amino or amino that is substituted by lower alkyl optionally substituted by phenyl, the N-terminal radical of a naturally occurring amino acid or the (D)-isomer thereof, or of a peptide consisting of from 2 to 6 naturally occurring amino acids and/or the (D)-isomers thereof, any free functional groups in such amino acids optionally being in protected form, free hydroxy or lower alkoxy, and salts of such compounds having salt-forming groups.

The invention relates most especially to the compounds of the formula I, mentioned above, in which amino and/or carboxy are present either as such or as optionally substituted benzyloxycarbonylamino or $C_1$-$C_{18}$-alkanoylamino and alkoxycarbonyl having from 1 to 18 carbon atoms, respectively, and salts of such compounds having salt-forming groups.

The invention relates primarily to compounds of the formula I in which $R^1$ represents hydrogen, the acyl radical of a naturally occurring amino acid, the acyl radical of a dipeptide consisting of naturally occurring amino acids, or lower alkanoyl, $R^2$ represents branched lower alkyl, $R^3$ represents free hydroxy, and $R^4$ represents free amino or amino substituted by lower alkyl or by benzyl, or the N-terminal radical of a naturally occurring amino acid or of a di- or tri-peptide consisting of such amino acids, and salts of such compounds having salt-forming groups.

Deserving of emphasis are compounds of the formula I in which $R^1$ represents the acyl radical of a dipeptide consisting of naturally occurring amino acids, $R^2$ represents 2-methylpropyl, $R^3$ represents free hydroxy, and $R^4$ represents the N-terminal radical of a di- or tri-peptide consisting of naturally occurring amino acids, with the exception of the compounds H-Pro-His-Pro-Phe-His-Sta-Leu-Phe-NH$_2$, N-isovaleryl-Pro-His-Pro-Phe-His-Sta-Leu-Phe-NH$_2$ and N-tert.-butoxycarbonyl-Pro-His-Pro-Phe-His-Sta-Leu-Phe-NH$_2$, and pharmaceutically acceptable salts of these compounds.

Especially deserving of emphasis are the compounds of the formula I, mentioned above, in which amino acid radicals occurring in the radicals $R^1$ and $R^4$ are derived from those 20 amino acids in their natural configuration which regularly occur in proteins, and pharmaceutically acceptable salts of these compounds.

Most especially deserving of emphasis are compounds of the formula I in which $R^1$ represents the radical H-Pro-His- or H-Ile-His-, $R^2$ represents 2-methylpropyl, $R^3$ represents free hydroxy, and $R^4$ represents the radical -Val-Tyr-Lys-OH, -Ile-His-Lys-OH, -Ile-His-Ser-OH, -Val-Tyr-Ser-OH, -Val-Tyr-OH, -Ile-His-OH, -Val-Tyr-NH$_2$, -Ile-His-NH$_2$ or -Ala-Sta-OH, and pharmaceutically acceptable salts of these compounds.

The invention relates especially to the compounds of the formula I, mentioned above, in which the abbreviations -Pro-, -Phe- and -His- used in the formula I represent the radicals of corresponding (L)-amino acids, and salts of such compounds having salt-forming groups.

Also preferred are the following compounds of the formula I and salts of such compounds having at least one salt-forming group in which (a) $R^1$ represents the radical H-Ile-His-, $R^2$ represents 2-methylpropyl, $R^3$ represents free hydroxy, and $R^4$ represents the radical -Val-Tyr-Lys-OH, -Ile-His-Lys-OH, -Ile-His-Ser-OH, -Val-Tyr-Ser-OH, -Val-Tyr-OH, -Ile-His-OH, -Val-Tyr-NH$_2$, -Ile-His-NH$_2$ or -Ala-Sta-OH, (b) $R^1$ represents the radical of a peptide consisting of at most 6 naturally occurring amino acids and/or the (D)-isomers thereof, any free functional groups in these radicals optionally being in protected form, $R^2$ represents lower alkyl or phenyl-lower alkyl, $R^3$ represents free hydroxy, and $R^4$ represents free amino or amino that is substituted by lower alkyl optionally substituted by phenyl, the N-terminal radical of a naturally occurring amino acid or the (D)-isomer thereof, or of a peptide consisting of from 2 to 6 naturally occurring amino acids and/or the (D)-isomers thereof, any free functional groups in such amino acids optionally being in protected form, free hydroxy or lower alkoxy, with the exception of the compounds H-Pro-His-Pro-Phe-His-Sta-Leu-Phe-NH$_2$, N-isovaleryl-Pro-His-Pro-Phe-His-Sta-Leu-Phe-NH$_2$ and N-tert.-butoxycarbonyl-Pro-His-Pro-Phe-His-Sta-Leu-Phe-NH$_2$, (c) $R^1$ represents the acyl radical of a dipeptide consisting of naturally occurring amino acids or lower alkanoyl, $R^2$ represents branched lower alkyl, $R^3$ represents free hydroxy, and $R^4$ represents free amino or amino substituted by lower alkyl or by benzyl, or the N-terminal radical of a naturally occurring amino acid or of a di- or tri-peptide consisting of such amino acids, with the exception of the compounds H-Pro-His-Pro-Phe-His-Sta-Leu-Phe-NH$_2$, N-isovaleryl-Pro-His-Pro-Phe-His-Sta-Leu-Phe-NH$_2$ and N-tert.-butoxycarbonyl-Pro-His-Pro-Phe-His-Sta-Leu-Phe-NH$_2$, (d) $R^1$ represents the acyl radical of a dipeptide consisting of two naturally occurring (L)-amino acids or the (D)-isomers thereof, the acyl radical of an oligopeptide having from 3 to 6 naturally occurring amino acids and at most 60 carbon atoms, any free functional groups in these amino acid radicals optionally being in protected form, or another aliphatic, aromatic or aromatic-aliphatic acyl radical having up to 18 carbon atoms which is different from the acyl radical of N-unsubstituted or N-substituted (L)- or (D)-histidine or sarcosine, $R^2$ represents alkyl or aralkyl, $R^3$ represents free or functionally modified hydroxy, $R^4$ represents free or substituted amino or free or etherified hydroxy, and -Pro-, -Phe- and -His- respectively represent the bivalent radicals of the amino acids proline, phenylalanine and histidine or the (D)-isomers thereof, with the exception of the compounds (H, Boc or isovaleryl)-Pro-His-Pro-Phe-His-Sta-Leu-Phe-NH$_2$ and (H, Boc, acetyl or phenoxyacetyl)-Pro-Phe-His-Sta-Leu-Phe-NH$_2$, (e) $R^1$ represents the acyl radical of a dipeptide consisting of two naturally occurring (L)-amino acids or the (D)-isomers thereof, the acyl radical of an oligopeptide having from 3 to 6 naturally occurring amino acids and at most 60 carbon atoms, any free functional groups in these amino acid radicals optionally being in protected form, or another aliphatic, aromatic or aromatic-aliphatic acyl radical having up to 18 carbon atoms which is different from the acyl radical of N-unsubstituted or N-substituted (L)- or (D)-histidine or sarcosine, $R^2$ represents alkyl or aralkyl each of which has not more than 18 carbon atoms, $R^3$ represents free of esterified hydroxy having at most 18 carbon atoms, and $R^4$ represents free amino or amino substituted by aryl-lower alkyl having at most 18 carbon atoms or by lower alkyl, the N-terminal radical of a naturally occurring amino acid or the (D)-isomer thereof, or of a peptide consisting of from 2 to 6 naturally occurring amino acids and/or the (D)-isomers thereof, any free functional groups in such amino acids being optionally in protected from, or free or etherified hydroxy having at most 12 carbon atoms, with the exception of the compounds (H, Boc or isovaleryl)-Pro-His-Pro-Phe-His-Sta-Leu-Phe-$NH_2$ and (H, Boc, acetyl or phenoxyacetyl)-Pro-Phe-His-Sta-Leu-Phe-$NH_2$, and also compounds of the formula I from the classes mentioned above, and salts of such compounds having salt-forming groups, that contain at least two amino acids that are different from $\alpha$-amino acids, especially two statin molecules, for example those compounds which have the sequence -Sta-Ala-Sta-, -Sta-Gly-Sta-, -Sta-Ile-Sta-, -Sta-Sta- or -Sta-Sar-Sta, or compounds that contain $\beta$-alanine, for example the sequence -Sta-$\beta$-Ala-His, or $\gamma$-aminobutyric acid, and also compounds of the formula I that have at least one hydroxycarboxylic acid, for example (L)-lactic acid or glycolic acid, in place of an amino acid, for example in the radical $R^4$ next to the $\gamma$-amino acid, and also compounds of the formula I in which $R^1$ represents the radical H-Arg-Arg- the N-terminal amino acid of which is optionally in protected form, for example compounds in which $R^1$ represents the radical Z-Arg-Arg-.

The invention relates above all to the compounds of the formula I mentioned in the Examples, especially Z-Arg-Arg-Pro-Phe-His-Sta-Ile-His-Lys(Boc)-$OCH_3$, and their pharmaceutically acceptable salts.

The compounds of the formula I according to the invention and salts of such compounds having at least one salt-forming group are obtained according to processes known per se, for example by (a) producing an amide bond of a compound of the formula I by reacting a corresponding fragment having a free carboxy group or a reactive acid derivative thereof with a complementary fragment having a free amino group or with a reactive derivative thereof having an activated amino group, any free functional groups in the reactants, with the exception of those groups participating in the above-mentioned reaction, being optionally in protected form, and, if necessary, removing any protecting groups or (b) for the manufacture of compounds of the formula I in which $R^3$ represents free hydroxy, reducing the keto group in a compound of the formula II

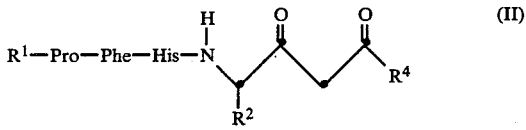

in which the substituents have the meanings given above, with the proviso that any free functional groups in the compound, with the exception of the keto group participating in the reaction, are optionally in protected form, by reaction with a regioselective reducing agent to form a hydroxy group and, if necessary, removing any protecting groups or (c) at the C=C double bond of a compound of the formula III

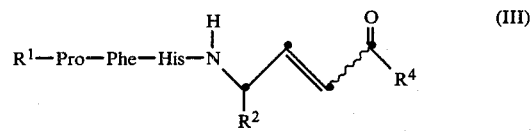

in which the substituents have the meanings given above, with the proviso that any free functional groups in the compound, with the exception of the double bond participating in the reaction, are optionally in protected form, adding regioselectively a compound of the formula $R^3$-H in which $R^3$ has the meaning given above and, if necessary, removing any protecting groups or (d) in a compound of the formula IV

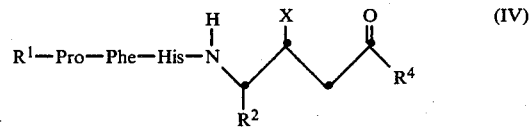

in which X represents a good leaving group and the other substituents have the meanings given above, with the proviso that any free functional groups in the compound, with the exception of the group participating in the reaction, are optionally in protected form, exchanging the substituent X, with a reagent that provides the substituent $R^3$ in nucleophilic form, for $R^3$ and, if necessary, removing any protecting groups or (e) for the manufacture of a compound of the formula I in which $R^4$ represents free or substituted amino, converting the cyano group in a compound of the formula V

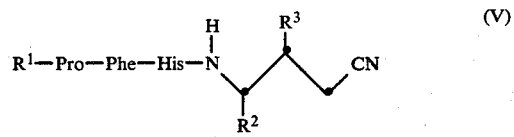

in which the substituents have the meanings given above into an optionally N-substituted amide group or (f) for the manufacture of a compound of the formula I in which $R^3$ represents free hydroxy, reducing an epoxide of the formula VI

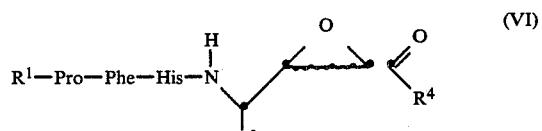

in which the substituents have the meanings given above, with the proviso that any free functional groups in the compound, with the exception of the epoxy group participating in the reaction, are optionally in protected form, with a regioselective reducing agent to form the corresponding alcohol and, if necessary, removing any protecting groups or (g) reacting, after activation with zinc (analogously to a Reformatsky reaction), a compound of the formula VII

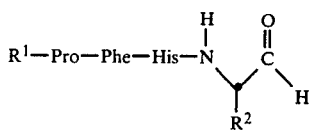

(VII)

in which the substituents have the meanings given above, with the proviso that any free functional groups in the compound, with the exception of the aldehyde group participating in the reaction, are optionally in protected form, with a compound of the formula VIII

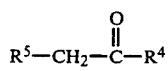

(VIII)

in which $R^5$ presents halogen having an atomic weight of between 35 and 127 and $R^4$ has the meaning given above, with the proviso that any free functional groups in a compound of the formula VIII, with the exception of the group participating in the reaction, are optionally in protected form, and, if necessary, removing any protecting groups or (h) in a compound of the formula I in which the substituents have the meanings given above, with the proviso that in a compound of the formula I at least one free amino, hydroxy, mercapto or carboxy group is present and the other functional groups are optionally in protected form, acylating at least one free amino, hydroxy or mercapto group with a carboxylic acid containing the radical to be introduced or with a reactive derivative thereof, or esterifying at least one free carboxy group or a reactive derivative thereof, and, if necessary, removing any protecting groups or (i) in a compound of the formula I in which the substituents have the meanings given above, with the proviso that in a compound of the formula I at least one free amino, hydroxy or mercapto group is present and the other functional groups are optionally in protected form, alkylating at least one free amino group, or etherifying a free hydroxy or mercapto group, and, if necessary, removing any protecting groups or (j) for the manufacture of a compound of the formula I in which $R^4$ represents the N-terminal radical of an optionally correspondingly substituted amino acid, cleaving a lactone of the formula IX

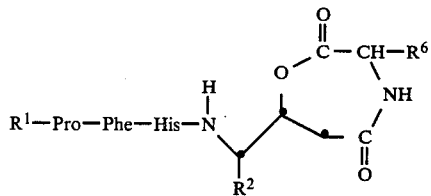

(IX)

in which $R^1$ and $R^2$ have the meanings given above and $R^6$ represents the corresponding radical in a naturally occurring amino acid of the formula X or the (D)-isomer thereof

(X)

which can be linked amidically via a carboxy or amino group in the radical $R^6$ with a further naturally occurring amino acid or with a peptide consisting of from 2 to 5 naturally occurring amino acids or the (D)-isomers thereof, any free functional groups in these amino acid radicals being optionally in modified form, or (k) for the manufacture of a compound having at least one free functional group in a compound of the formula I in which the substituents have the meanings given above, with the proviso that in a compound of the formula I at least one functional group is protected by a readily removable protecting group, removing the protecting groups present, optionally in stages, and, if desired, after carrying out one of the processes (a) to (k) mentioned above or any other process for the manufacture of a compound of the formula I, converting a resulting compound of the formula I having at least one salt-forming group into its salt or converting a resulting salt into the free compound or into a different salt and-/or separating stereoisomeric mixtures which may or may not be obtained and/or epimerising a resulting compound of the formula I.

The removal of a protecting group at the end of the process variants (a)–(d) and (f)–(i) is necessary if the desired product does contain the protecting group in question.

The invention relates also to the compounds obtainable in accordance with any one of the above-mentioned processes, and to the salts thereof.

Process (a)

(Production of an amide bond)

Reactive carboxylic acid derivatives of a fragment of a compound of the formula I having a free carboxy group are especially activated esters or reactive anhydrides, and also reactive cyclic amides; reactive acid derivatives may also be formed in situ.

Activated esters of acids are especially esters that are unsaturated at the linking carbon atom of the esterifying radical, for example of the vinyl ester type, such as actual vinyl esters (which can be obtained, for example, by transesterification of a corresponding ester with vinyl acetate; activated vinyl ester method), carbamoylvinyl esters (which can be obtained, for example, by treatment of the corresponding acid with an isoxazolium reagent; 1,2-oxazolium or Woodward method), or 1-lower alkoxyvinyl esters (which can be obtained, for example, by treatment of the corresponding acid with a lower alkoxyacetylene; ethoxyacetylene method), or esters of the amidino type, such as N,N'-disubstituted amidino esters (which can be obtained, for example, by treatment of the corresponding acid with a suitable N,N'-disubstituted carbodiimide, for example N,N'-dicyclohexyl carbodiimide; carbodiimide method), or N,N-disubstituted amidino esters (which can be obtained, for example, by treatment of the corresponding acid with an N,N-disubstituted cyanamide; cyanamide method), suitable aryl esters, especially phenyl esters suitably substituted by electron-attracting substituents (which can be obtained, for example, by treatment of the corresponding acid with a suitably substituted phenol, for example 4-nitrophenol, 4- methylsulphonylphenol, 2,4,5-trichlorophenol, 2,3,4,5,6-pentachlorophenol or 4-phenyldiazophenol, in the presence of a condensation agent, such as N,N'-dicyclohexyl carbodiimide; activated aryl esters method), cyanomethyl esters (which can be obtained, for example, by treatment of the corresponding acid with chloroacetonitrile in the presence of a base; cyanomethyl esters method), thioesters, especially phenylthioesters optionally substituted, for example, by nitro (which can be obtained, for example, by treatment of the corresponding acid with thiophenols that are optionally substituted, for example, by nitro inter alia with the aid of the anhydride or carbodiimide method; activated thioesters method), or amino or amido esters (which can be obtained, for example, by treatment of the corresponding acid with an N-hydroxyamino or N-hydroxyamido compound, for example N-hydroxysuccinimide, N-hydroxypiperidine, N-hydroxyphthalimide, N-hydroxy-5-norbornene-2,3-dicarboxylic acid imide or 1-hydroxybenzotriazole, for example according to the anhydride or carbodiimide method; activated N-hydroxy esters method).

Anhydrides of acids, may be symmetric or preferably mixed anhydrides of these acids, thus, for example, anhydrides with inorganic acids, such as acid halides, especially acid chlorides (which can be obtained, for example, by treating the corresponding acid with thionyl chloride, phosphorus pentachloride or oxalyl chloride; acid chloride method), azides (which can be obtained, for example, from a corresponding acid ester by way of the corresponding hydrazide and the treatment of the latter with nitrous acid; azide method), anhydrides with carbonic acid semi-derivatives, such as with corresponding esters, for example carbonic acid lower alkyl semi-esters (which can be obtained, for example, by treating the corresponding acid with haloformic acid lower alkyl esters, such as chloroformic acid lower alkyl esters, or with a 1-lower alkoxycarbonyl-2-lower alkoxy-1,2-dihydroquinoline, for example 1-lower alkoxycarbonyl-2-ethoxy-1,2-dihydroquinoline; mixed 0-alkylcarbonic acid anhydrides method), or anhydrides with dihalogenated, especially dichlorinated, phosphoric acid (which can be obtained, for example, by treating the corresponding acid with phosphorus oxychloride; phosphorus oxychloride method), anhydrides with other phosphoric acid derivatives (for example those which can be obtained with phenyl-N-phenylphosphoramidochloridate) or with phosphorous acid derivatives, or anhydrides with organic acids, such as mixed anhydrides with organic carboxylic acids (which can be obtained, for example, by treating the corresponding acid with an optionally substituted lower alkanecarboxylic acid halide or phenylalkanecarboxylic acid halide, for example phenylacetic acid chloride, pivalic acid chloride or trifluoroacetic acid chloride; mixed carboxylic acid anhydrides method) or with organic sulphonic acids (which can be obtained, for example, by treating a salt, such as an alkali metal salt, of the corresponding acid, with a suitable organic sulphonic acid halide, such as lower alkanesulphonic acid chloride or arylsulphonic acid chloride, for example methane- or p-toluene-sulphonic acid chloride; mixed sulphonic acid anhydrides method), and symmetric anhydrides (which can be obtained, for example, by condensing the corresponding acid in the presence of a carbodiimide or of 1-diethylaminopropine; symmetric anhydrides method).

Suitable cyclic amides are especially amides having five-membered diazacycles of aromatic character, such as amides with imidazoles, for example imidazole (which can be obtained, for example, by treating the corresponding acid with N,N'-carbonyldiimidazole; imidazolide method), or pyrazoles, for example 3,5-dimethylpyrazole (which can be obtained, for example, by way of the acid hydrazide by treatment with acetylacetone; pyrazolide method).

A complementary fragment having a free amino group is ammonia or a primary or secondary amine.

The amino group participating in the reaction in a complementary fragment of a compound of the formula I is preferably in free form, especially if the carboxy group reacting therewith is in reactive form; it can also, however, itself be a derivative, that is to say, for example, it can have been activated by reaction with a phosphite, such as diethylchlorophosphite, 1,2-phenylenechlorophosphite, ethyldichlorophosphite, ethylenechlorophosphite or tetraethylpyrophosphite. A reactive form of such a complementary fragment is, for example, also a carbamic acid halide or an isocyanate, the amino group participating in the reaction being bonded to halocarbonyl, for example chlorocarbonyl, or being in the form of an isocyanate group, it being possible, in the latter case, to obtain only compounds of the formula I that have a hydrogen atom at the nitrogen atom of the amide group formed by the reaction.

If the complementary fragment having a free amino group is ammonia or an amine that is mono- or disubstituted by lower alkyl or aryl-lower alkyl, a corresponding urea also constitutes a reactive form. For example, on heating equimolar amounts of such a urea and the component having a free carboxy group, corresponding compounds of the formula I are obtained in good yield.

If the complementary fragment is dimethylamine, for example dimethylformamide also constitutes a reactive form thereof.

Protecting groups of any functional groups that may optionally be present are, for example, the protecting groups mentioned above.

The reaction can be carried out in a manner known per se, the reaction conditions depending especially on whether and how the carboxy group participating in the reaction has been activated, usually in the presence of a suitable solvent or diluent or a mixture thereof and, if necessary, in the presence of a condensation agent which, for example if the carboxy group participating in the reaction is in the form of an anhydride, can also be an acid-binding agent, while cooling or heating, for example within a temperature range of from approximately $-30°$ to approximately $+200°$ C., in a closed reaction vessel and/or in the atmosphere of an inert gas, for example nitrogen.

Customary condensation agents are, for example, carbodiimides, for example N,N'-diethyl, N,N'-dipropyl, N,N'-dicyclohexyl or N-ethyl-N'-(3-dimethylaminopropyl) carbodiimide, suitable carbonyl compounds, for example carbonyl diimidazole, or 1,2-oxazolium compounds, for example 2-ethyl-5-phenyl-1,2-oxazolium 3'-sulphonate and 2-tert.-butyl-5-methylisoxazolium perchlorate, or a suitable acylamino compound, for example 2-ethoxy-1-ethoxycarbonyl-1,2-dihydroquinoline. Customary acid-binding condensation agents are, for example, alkali metal carbonates or bicarbonates, for example sodium or potassium carbonate or sodium or potassium bicarbonate (usually together with a sulphate), or organic bases, such as usually sterically hindered tri-lower alkylamines, for example N,N-diisopropyl-N-ethylamine.

As already mentioned, reactive acid derivatives may also be formed in situ. Thus, for example, N,N'-disubstituted amidino esters can be formed in situ by reacting the mixture of the fragment having a free carboxy group and the complementary fragment having a free amino group in the presence of a suitable N,N'-disubstituted carbodiimide, for example N,N'-dicyclohexyl carbodiimide. Amino or amido esters of such acids can also be formed in the presence of the amino component to be acylated, by reacting the mixture of the corresponding acid and amino starting materials in the presence of an N,N'-disubstituted carbodiimide, for example N,N'-dicyclohexyl carbodiimide, and an N-hydroxyamine or N-hydroxyamide, for example N-hydroxysuccinimide, optionally in the presence of a suitable base, for example 4-dimethylaminopyridine.

The starting materials for carrying out process (a) are known or can be manufactured according to processes known per se, for example from the relevant amino acids analogously to the process described above.

Process (b)

(Reduction of a keto group).

The regioselective reducing agents that can be used are those which, under the reaction conditions, reduce an isolated keto group sufficiently more rapidly than amide groups.

There are to be mentioned especially suitable borohydrides, such as alkali metal borohydrides, especially sodium borohydride, lithium borohydride or sodium cyanoborohydride, or suitable aluminium hydrides, such as sterically hindered alkali metal lower alkoxyaluminium hydrides, for example lithium tris-tert.-butoxyaluminium hydride.

Reduction can also be carried out with hydrogen in the presence of suitable heavy metal catalysts, for example Raney nickel, platinum or palladium catalysts, or according to the Meerwein-Ponndorf-Verley method with the aid of aluminium alkanolates, preferably aluminium 2-propanolate or ethanolate.

The reduction can be carried out preferably with stoichiometric amounts or, if necessary owing to undesired side reactions, for example with the solvent, with a reasonably proportioned excess of the reducing agent, in an inert solvent at temperatures of between $-80°$ and $+180°$ C., preferably between $-20°$ and $+100°$ C., if necessary under a protective gas, for example argon.

The starting ketones of the formula II can be obtained according to processes known per se, for example by Claisen condensation of an ester, for example the ethyl ester, of an acid of the formula XI

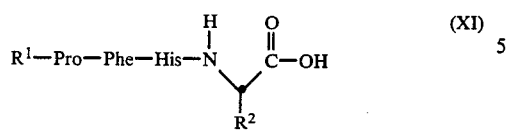

in which the substituents have the meanings given above, with the proviso that any free functional groups in the compound, with the exception of the ester group participating in the reaction, are optionally in protected form, with an acetic acid ester, amidation of the resulting ester with an amine $R^4$-H and subsequent removal of the protecting groups.

Alternatively a corresponding γ-amino-β-oxocarboxylic acid obtainable by Claisen condensation can be incorporated into the peptide chain according to the methods described in process (a).

Process (c)

(Addition to an olefin).

The compound of the formula $R^3$-H is, depending on the meaning of $R^3$, for example, water, an alcohol, a carboxylic acid or a hydrohalic acid. The reaction is preferably carried out with acidic or basic catalysis.

The starting olefin of the formula III can be obtained according to methods known per se, for example by incorporating an α,β-unsaturated amino acid of the formula XII

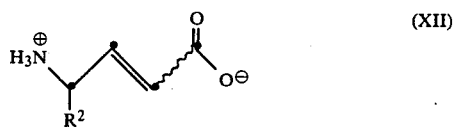

in which $R^2$ has the meaning given above, into the peptide chain according to the methods described in process (a).

The amino acid of the formula XII is obtainable, for example, from an α-aminoaldehyde that is optionally in protected form and a malonic acid derivative, for example malodinitrile or malonic acid diethyl ester, by the Knoevenagel-Doebner method.

Process (d)

(Nucleophilic substitution).

A leaving group X is especially hydroxy esterified by a strong inorganic or organic acid, such as a mineral acid, for example a hydrohalic acid, such as hydrochloric acid, hydrobromic acid or hydriodic acid, and also sulphuric acid, or a halosulphuric acid, for example fluorosulphuric acid, or is hydroxy esterified by a strong organic sulphonic acid, such as a lower alkanesulphonic acid that is optionally substituted, for example by halogen, such as fluorine, or an aromatic sulphonic acid, for example a benzenesulphonic acid that is optionally substituted by lower alkyl, such as methyl, halogen, such as bromine, and/or by nitro, for example a methanesulphonic, trifluoromethanesulphonic or p-toluenesulphonic acid, or is hydroxy esterified by hydrazoic acid.

A reagent that provides the substituent $R^3$ in nucleophilic form is, depending on the meaning of $R^3$, for example water, an alcohol or the salt of a carboxylic acid.

The reaction conditions are preferably so chosen that the reaction proceeds substantially as a second order nucleophilic substitution. For example, a compound of the formula IV in which X represents a leaving group of high polarisability, for example iodine, can be reacted in a dipolar aprotic solvent, for example acetone, acetonitrile, nitromethane or dimethylformamide, with the caesium salt of a carboxylic acid.

Process (d)

(Conversion of a cyano group into an amide group).

Conversion can be effected by partial hydrolysis, the manner of a Graf-Ritter reaction or by way of carboxylic acid ester imide salts. The conditions for the hydrolysis of a compound of the formula V must be so chosen that the reaction can be held at the amide stage and does not proceed to the free carboxylic acid. Most generally suitable for this purpose is hydrolysis with acids, it being possible, depending on the substituents present in a compound of the formula V, especially to choose between 80% sulphuric acid (with heating), polyphosphoric acid (at 110°–150°), hydrogen bromide/ glacial acetic acid (room temperature), formic acid (without solvent), hydrogen chloride gas in ethereal solution followed by the addition of water or aqueous hydrochloric acid, or boron halides/1 equivalent of water.

In some cases, alkaline hydrolysis, especially according to the Radziszewski method with hydrogen peroxide in the presence of alkalis at moderate temperature, is also successful.

The manufacture of N-substituted amides from the nitriles of the formula V can be carried out successfully with the aid of the Graf-Ritter reaction. For this purpose, the nitriles are reacted in the presence of a strong acid, especially 85–90% sulphuric acid, or also polyphosphoric acid, formic acid, boron trifluoride or other Lewis acids, but not aluminium chloride, with compounds that are capable of forming in the acidic medium carbenium ions, that is to say, for example, with olefins, such as propylene, or alcohols, such as benzyl alcohol.

In accordance with a variant of the Graf-Ritter reaction, the reaction may also be catalysed by mercury(II) nitrate followed by reduction with sodium borohydride.

The carboxylic acid ester imides are obtained, for example, by acid-catalysed addition of alcohols to the nitriles. The amides are obtained from the ester imides in the manner of a Pinner cleavage by thermal decomposition of the ester imide salts at temperatures above approximately 80° C.

Nitriles of the formula V can be manufactured, for example, by a Kolbe synthesis from the corresponding primary halides with cyanide ions in the manner of a nucleophilic substitution. Alternatively, a compound of the formula XIII

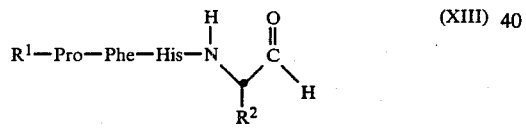

in which the substituents have the meanings given above, with the proviso that any free functional groups in the compound, with the exception of the aldehyde group participating in the reaction, are optionally in protected form, can be reacted with preferably an excess of acetonitrile in the presence of preferably catalytic amounts of a strong base.

Process (f)

(Reduction of an epoxide).

The regioselective reducing agents that can be used are those which, under the reaction conditions, reduce an epoxy group sufficiently more rapidly than amide groups and open the epoxide in such a manner that a sufficient, and as large as possible, proportion of the reaction product carries the newly formed hydroxy group in the position corresponding to that of the formula I, for example lithium borohydride or sodium cyanoborohydride/boron trifluoride etherate.

Using the last-mentioned reagent the reaction can be carried out, for example, by adding a solution of boron trifluoride etherate, $BF_3.O(C_2H_5)_2$, in tetrahydrofuran to 1 mole of the compound of the formula VI and an excess, for example 1.4–3 moles, of sodium cyanoborohydride in tetrahydrofuran at elevated temperature, for example under reflux, in such a manner that the pH of the reaction solution is maintained close to the turning point of the indicator bromocresol green.

The epoxide of the formula VI can be manufactured according to methods known per se, for example by epoxidation of an unsaturated amino acid of the formula XII and incorporation of the resulting amino acid into the peptide chain according to process (a).

Process (Reformatsky reaction).

The reaction can be carried out, for example, by first of all activating a compound of the formula VIII, for example one in which $R^5$ represents bromine, with preferably stoichiometric amounts of zinc in an alcohol at elevated temperature, for example in boiling methanol, and, if appropriate, having added tetrahydrofuran to increase the solubility, reacting the compound at a temperature of between approximately −30° and +60° C., preferably between 0° and +20° C., with the aldehyde of the formula VII.

The starting materials of the formula VII can be obtained according to methods known per se, for example by reduction of a corresponding acid chloride, for example with lithium tris-tert.-butoxyaluminium hydride or according to the Rosenmund method. It is also possible, for example using the corresponding amino acid as starting material, first of all to produce the terminal aminoaldehyde and then incorporate it into the peptide chain according to the methods described in process (a).

The starting materials of the formula VIII are also obtainable according to processes known per se, for example by amidation of the corresponding α-haloacetic acid, as described in process (a).

Process (h)

(Acylation).

The reactive derivative of a carboxylic acid that is used as acylating agent is, for example, one of those mentioned in process (a).

The reactive derivative of a carboxy group to be esterified in a compound of the formula I is, for example, one of those mentioned in process (a) or a reactive salt, for example a caesium salt.

For esterification of a carboxy group in a compound of the formula I either the free acid or preferably one of the reactive carboxylic acid derivatives mentioned in process (a) can be reacted with an alcohol, or the free acid or a reactive carboxylic acid salt can be reacted with an esterifying agent, for example a reactive derivative of an alcohol. For example the caesium salt of a carboxylic acid can be reacted with a halide.

Suitable agents for esterifying a carboxy group in a compound of the formula I are, for example, corresponding diazo compounds, such as optionally substituted diazo-lower alkanes, for example diazomethane, diazoethane, diazo-n-butane or diphenyldiazomethane. These reagents are used in the presence of a suitable inert solvent, such as an aliphatic, cycloaliphatic or aromatic hydrocarbon, such as hexane, cyclohexane, benzene or toluene, a halogenated aliphatic hydrocarbon, for example methylene chloride, or an ether, such as a di-lower alkyl ether, for example diethyl ether, or a cyclic ether, for example tetrahydrofuran or dioxan, or a solvent mixture, and, depending on the diazo reagent, while cooling, at room temperature or while heating slightly, and also, if necessary, in a closed vessel and/or under an inert gas atmosphere, for example a nitrogen atmosphere.

Further suitable agents for esterifying a carboxy group in a compound of the formula I are esters of corresponding alcohols, especially those with strong inorganic or organic acids, such as mineral acids, for example hydrohalic acids, such as hydrochloric acid, hydrobromic acid or hydriodic acid, also sulphuric acid, or halosulphuric acids, for example fluorosulphuric acid, or strong organic sulphonic acids, such as lower alkanesulphonic acids that are optionally substituted, for example by halogen, such as fluorine, or aromatic sulphonic acids such as, for example, benzenesulphonic acids that are optionally substituted by lower alkyl, such as methyl, halogen, such as bromine, and/or by nitro, for example methanesulphonic acid, trifluoromethanesulphonic acid or p-toluenesulphonic acid. Such esters are, inter alia, lower alkyl halides, di-lower alkyl sulphates, such as dimethyl sulphate, also fluorosulphonic acid esters, such as fluorosulphonic acid lower alkyl esters, for example fluorosulphonic acid methyl ester, or optionally halo-substituted methanesulphonic acid lower alkyl esters, for example trifluoromethanesulphonic acid methyl ester. They are usually used in the presence of an inert solvent, such as an optionally halogenated, such as chlorinated, aliphatic, cycloaliphatic or aromatic hydrocarbon, for example methylene chloride, an ether, such as dioxan or tetrahydrofuran, or a mixture thereof. At the same time, there are preferably used suitable condensation agents, such as alkali metal carbonates or bicarbonates, for example sodium or potassium carbonate or sodium or potassium bicarbonate (usually together with a sulphate), or organic bases, such as usually sterically hindered tri-lower alkylamines, for example N,N-diisopropyl-N-ethylamine (preferably together with halosulphonic acid lower alkyl esters or optionally halo-substituted methanesulphonic acid lower alkyl esters), the reaction being carried out while cooling, at room temperature or while heating, for example at temperatures of from approximately −20° to approximately +50° C. and, if necessary, in a closed vessel and/or in an inert gas atmosphere, for example a nitrogen atmosphere.

Further agents for esterifying a carboxy group in a compound of the formula I are corresponding trisubstituted oxonium salts (so-called Meerwein salts), or disubstituted carbenium or halonium salts in which the substituents are the esterifying radicals, for example tri-lower alkyloxonium salts, and also di-lower alkoxycarbenium or di-lower alkylhalonium salts, especially the corresponding salts with complex fluorine-containing acids, such as the corresponding tetrafluoroborates, hexafluorophosphates, hexafluoroantimonates or hexachloroantimonates. Such reagents are, for example, trimethyloxonium hexafluoroantimonate, hexachloroantimonate, hexafluorophosphate or tetrafluoroborate or triethyloxonium hexafluoroantimonate, hexachloroantimonate, hexafluorophosphate or tetrafluoroborate, dimethoxycarbenium hexafluorophosphate or dimethylbromonium hexafluoroantimonate. These esterifying agents are used preferably in an inert solvent, such as an ether or a halogenated hydrocarbon, for example diethyl ether, tetrahydrofuran or methylene chloride, or in a mixture thereof, if necessary in the presence of a base, such as an organic base, for example a preferably sterically hindered tri-lower alkylamine, for example N,N-diisopropyl-N-ethylamine, and while cooling, at room temperature or while heating slightly, for example at from approximately −20° to approximately +50° C., if necessary in a closed vessel and/or in an inert gas atmosphere, for example a nitrogen atmosphere.

The esterification of free carboxy with the desired free alcohol is carried out in the presence of a suitable condensation agent. Customary condensation agents are, for example carbodiimides, for example N,N'-diethyl, N,N'-dipropyl, N,N'-dicyclohexyl or N-ethyl-N'-(3-dimethylaminopropyl) carbodiimide, suitable carbonyl compounds, for example carbonyl diimidazole, or 1,2-oxazolium compounds, for example 2-ethyl-5-phenyl-1,2-oxazolium 3'-sulphonate and 2-tert.-butyl-5-methyl-isoxazolium perchlorate, or a suitable acylamino compound, for example 2-ethoxy-1-ethoxycarbonyl-1,2-dihydroquinoline. The condensation reaction is carried out preferably in an anhydrous reaction medium, preferably in the presence of a solvent or diluent, for example methylene chloride, dimethylformamide, acetonitrile or tetrahydrofuran and, if necessary, while cooling or heating and/or in an inert gas atmosphere.

To acylate an amino, hydroxy or mercapto group in a compound of the formula I the starting material of the formula I is treated with an acylating agent that introduces the desired acyl radical of an organic carboxylic acid. In so doing, there is used the corresponding carboxylic acid or a reactive derivative thereof, especially an anhydride, including a mixed or internal anhydride, of such an acid. Mixed anhydrides are, for example, those with hydrohalic acids, i.e. the corresponding acid halides, especially acid chlorides, and also with hydrocyanic acid, or alternatively those with suitable carbonic acid semi-derivatives, such as corresponding carbonic acid semi-esters (such as the mixed anhydrides formed with, for example, a haloformic acid lower alkyl ester, such as chloroformic acid ethyl ester or isobutyl ester), or with optionally substituted lower alkanecarboxylic acids, for example lower alkanecarboxylic acids containing halogen, such as chlorine (such as the mixed anhydrides formed with pivaloyl chloride or trichloroacetyl chloride). Internal anhydrides are, for example, those of organic carboxylic acids, i.e. ketenes, such as ketene or diketene, or those of carbamic or thiocarbamic acids, i.e. isocyanates or isothiocyanates. Further reactive derivatives of organic carboxylic acids which can be used as acylating agents are activated esters, such as suitably substituted lower alkyl esters, for example cyanomethyl ester, or suitably substituted phenyl esters, for example pentachlorophenyl ester or 4-nitrophenyl ester. The esterification can, if necessary, be carried out in the presence of suitable condensation agents, for example in the presence of carbodiimide compounds, such as dicyclohexyl carbodiimide, or carbonyl compounds, such as diimidazolylcarbonyl, when using free carboxylic acids, or, for example in the presence of basic agents, such as tri-lower alkylamines, for example triethylamine, or heterocyclic bases, for example pyridine, when using reactive acid derivatives. The acylation reaction can be carried out in the absence or presence of a solvent or solvent mixture, while cooling, at room temperature of while heating, and, if necessary, in a closed vessel and/or in an inert gas atmosphere, for example a nitrogen atmosphere. Suitable solvents are, for example, optionally substituted, especially optionally chlorinated, aliphatic, cycloaliphatic or aromatic hydrocarbons, such as benzene or toluene, it being possible to use suitable esterification reagents, such as acetyl anhydrides, also as diluents.

Process (i)

(Alkylation or etherification).

Suitable agents for alkylating an amino group or for etherifying a free hydroxy or mercapto group in a compound of the formula I are, for example, corresponding diazo compounds, such as optionally substituted diazo-lower alkanes, for example diazomethane, diazo-ethane, diazo-n-butane or diphenyldiazomethane. These reagents are used in the presence of a suitable inert solvent, such as an aliphatic, cycloaliphatic or aromatic hydrocarbon, such as hexane, cyclohexane, benzene or toluene, a halogenated aliphatic hydrocarbon, for example methylene chloride, or an ether, such as a di-lower alkyl ether, for example diethyl ether, or a cyclic ether, for example tetrahydrofuran or dioxan, or a solvent mixture and, depending on the diazo reagent, while cooling, at room temperature or while heating slighlty, and also, if necessary, in a closed vessel and/or under an inert gas atmosphere, for example a nitrogen atmosphere.

Further suitable agents are esters of corresonding alcohols, especially those with strong inorganic or organic acids, such as mineral acids, for example hydrohalic acids, such as hydrochloric acid, hydrobromic acid or hydriodic acid, also sulphuric acid, or halosulphuric acids, for example fluorosulphuric acid, or strong organic sulphonic acids, such as lower alkanesulphonic acids that are optionally substituted, for example by halogen, such as fluorine, or aromatic sulphonic acids, such as, for example, benzenesulphonic acids that are optionally substituted by lower alkyl, such as methyl, halogen, such as bromine, and/or by nitro, for example methanesulphonic acid, trifluoromethanesulphonic acid or p-toluenesulphonic acid. Such esters are, inter alia, lower alkyl halides, di-lower alkyl sulphates, such as dimethyl sulphate, also fluorosulphonic acid esters, such as fluorosulphonic acid lower alkyl esters, for example fluorosulphonic acid methyl ester, or optionally halo-substituted methanesulphonic acid lower alkyl esters, for example trifluoromethanesulphonic acid methyl ester. They are usually used in the presence of an inert solvent, such as an optionally halogenated aliphatic, cycloaliphatic or aromatic hydrocarbon, for example methylene chloride, an ether, such as dioxan or tetrahydrofuran, or a mixture thereof. In so doing there are preferably used suitable condensation agents, such as alkali metal carbonates or bicarbonates, for example sodium or potassium carbonate or sodium or potassium bicarbonate (usually together with a sulphate), or organic bases, such as usually sterically hindered tri-lower alkylamines, for example N,N-diisopropyl-N-ethylamine (preferably together with halosulphonic acid lower alkyl esters or optionally halo-substituted methanesulponic acid lower alkyl esters), the process being carried out while cooling, at room temperature or while heating, for example at temperatures of from approximately −20° to approximately 50° C. and, if necessary, in a closed vessel and/or in an inert gas atmosphere, for example a nitrogen atmosphere.

The etherification reaction described above can be considerably accelerated by phase transfer catalysis [see, for example, Dehmlow, Angewandte Chemie, 86, 187 (1974)]. As phase transfer catalysts there may be used quaternary phosphonium salts and especially quaternary ammonium salts, such as optionally substituted tetraalkylammonium halides, for example tetrabutylammonium chloride, bromide or iodide, or alternatively benzyltriethylammonium chloride, in catalytic amounts or up to equimolar amounts. Any of the solvents which is not miscible with water can be used as organic phase, for example one of the optionally halogenated, such as chlorinated, lower aliphatic, cycloaliphatic or aromatic hydrocarbons, such as tri- or tetrachloroethylene, tetrachloroethane, carbon tetrachloride, chlorobenzene, toluene or xylene. The alkali metal carbonates and bicarbonates, for example potassium or sodium carbonate or potassium or sodium bicarbonate, alkali metal phosphates, for example potassium phosphate, and alkali metal hydroxides, for example sodium hydroxide, that are suitable as condensation agents can, in the case of compounds that are sensitive to bases, be added to the reaction mixture titrimetrically, for example by means of an automatic titrating apparatus, so that, during etherification, the pH remains between approximately 7 and approximately 8.5.

Further agents are corresponding tri-substituted oxonium salts (so-called Meerwein salts), or disubstituted carbenium or halonium salts in which the substituents are the etherifying radicals, for example tri-lower alkyloxonium salts, and di-lower alkoxycarbenium or di-lower alkylhalonium salts, especially the corresponding salts with complex fluorine-containing acids, such as the corresponding tetrafluoroborates, hexafluorophosphates, hexafluoroantimonates or hexachloroantimonates. Such reagents are, for example, trimethyloxonium hexafluoroantimonate, hexachloroantimonate, hexafluorophosphate or tetrafluoroborate, triethyloxonium hexafluoroantimonate, hexachloroantimonate, hexafluorophosphate or tetrafluoroborate, dimethoxycarbenium hexafluorophosphate or dimethylbromonium hexafluoroantimonate. These etherifying agents are used preferably in an inert solvent, such as an ether or a halogenated hydrocarbon, for example diethyl ether, tetrahydrofuran or methylene chloride, or in a mixture thereof, if necessary in the presence of a base, such as an organic base, for example a preferably sterically hindered trilower alkylamine, for example N,N'-diisopropyl-N-ethylamine, and while cooling, at room temperature or while heating slightly, for example at from approximately −20° to approximately 50° C. if necessary in a closed vessel and/or in an inert gas atmosphere, for example a nitrogen atmosphere.

Further suitable etherifying agents are finally corresponding 1-substituted 3-aryltriazene compounds in which the substituent is the etherifying radical, and aryl represents preferably optionally substituted phenyl, for example lower alkylphenyl, such as 4-methylphenyl. Such triazene compounds are 3-aryl-1-lower alkyltriazenes, for example 3-(4-methylphenyl)-1-methyltriazene, 3-(4-methylphenyl)-1-ethyltriazene or 3-(4-methylphenyl)-1-isopropyltriazene. These reagents are usually used in the presence of inert solvents, such as optionally halogenated hydrocarbons or ethers, for example benzene, or solvent mixtures, and while cooling, at room temperature or preferably at elevated temperature, for example at from approximately 20°0 to approximately 100° C., if necessary in a closed vessel and/or in an inert gas atmosphere, for example a nitrogen atmosphere.

Process (j)

(Lactone opening).

The ring-opening of a lactone of the formula IX is achieved by mild acidic or alkaline treatment, for example with an alkali metal cyanide, such as sodium cyanide, or an alkali metal bisulphite, for example sodium bisulphite.

The starting materials of the formula IX can be obtained according to methods known per se, for example by the incorporation of a corresponding fragment, for example one of the formula XIV

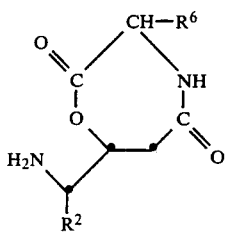

into the peptide chain according to the methods described in (a). The compound of the formula XIV can in its turn be obtained, for example, by cyclising a corresponding hydroxycarboxylic acid, preferably in highly diluted solution, or, using as starting material a corresponding ketone of the formula XV

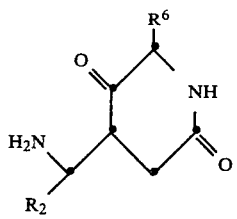

in which the amino group and optionally other functional groups are in protected form, by oxidation with a peroxy acid according to the Baeyer-Villiger method, especially with Caro's acid, $H_2SO_5$, according to the Ruzicka method.

Process (k)

(Removal of protecting groups).

Protecting groups of optionally present functional groups are, for example, the protecting groups mentioned hereinbefore.

These groups, for example protected carboxy, amino, hydroxy and/or mercapto groups, are freed in a manner known per se, optionally in stages or simultaneously, by means of solvolysis (also enzymatically), especially hydrolysis, alcoholysis or acidolysis, or by means of reduction, especially hydrogenolysis, or chemical reduction.

Thus, tert.-lower alkoxycarbonyl, or lower alkoxycarbonyl substituted in the 2-position by an organic silyl group or in the 1-position by lower alkoxy or lower alkylthio, or optionally substituted diphenylmethoxycarbonyl, can be converted into free carboxy, for example, by treatment with a suitable acid, such as formic acid or trifluoroacetic acid, optionally with the addition of a nucleophilic compound, such as phenol or anisole. Optionally substituted benzyloxycarbonyl can be freed, for example, by means of hydrogenolysis, that is to say by treatment with hydrogen in the presence of a metallic hydrogenation catalyst, such as a palladium catalyst. Furthermore, suitably substituted benzyloxycarbonyl, such as 4-nitrobenzyloxycarbonyl, can also be converted into free carboxy by means of chemical reduction, for example by treatment with an alkali metal dithionite, for example sodium dithionite, or with a reducing metal, for example tin, or a reducing metal salt, such as a chromium(II) salt, for example chromium(II) chloride, customarily in the presence of a hydrogen-yielding agent that together with the metal is capable of producing nascent hydrogen, such as an acid, especially a suitable carboxylic acid, such as a lower alkanecarboxylic acid optionally substituted, for example, by hydroxy, for example acetic acid, formic acid, glycolic acid, diphenylglycolic acid, lactic acid, mandelic acid, 4-chloromandelic acid or tartaric acid, or an alcohol or thiol, it being preferable to add water. By treatment with a reducing metal or metal salt, as described above, it is also possible to convert 2-halo-lower alkoxycarbonyl (optionally after converting a 2-bromo-lower alkoxycarbonyl group into a corresponding 2-iodo-lower alkoxycarbonyl group) or aroylmethoxycarbonyl into free carboxy, it being possible to cleave aroylmethoxycarbonyl likewise by treatment with a nucleophilic, preferably salt-forming, reagent, such as sodium thiophenolate or sodium iodide. Substituted 2-silylethoxycarbonyl can be converted into free carboxy also by treament with a salt of hydrofluoric acid that yields the fluoride anion, such as an alkali metal fluoride, for example sodium or potassium fluoride, in the presence of a macrocyclic polyether ("Crown ether"), or with a fluoride of an organic quaternary base, such as tetralower alkylammonium fluoride, or tri-lower alkylarylammonium fluoride, for example tetraethylammonium fluoride or tetrabutylammonium fluoride, in the presence of an aprotic polar solvent, such as dimethyl sulphoxide or N,N-dimethylacetamide. Carboxy esterified by an organic silyl group, such as tri-lower alkylsilyl, for example trimethylsilyl, can be freed in customary manner by solvolysis, for example by treatment with water, an alcohol or acid, or, moreover, with a fluoride, as described above. Esterified carboxy can also be cleaved enzymatically, for example esterified arginine or lysine, such as lysine methyl ester, can be cleaved by means of trypsin.

A protected amino group is freed in a manner known per se and, depending on the nature of the protecting groups, in various ways, preferably by means of solvolysis or reduction. 2-Halo-lower alkoxycarbonylamino (optionally after converting a 2-bromo-lower alkoxycarbonylamino group into a 2-iodo-lower alkoxycarbonylamino group), aroylmethoxycarbonylamino or 4-nitrobenzyloxycarbonylamino can be cleaved, for example, by treatment with a suitable chemical reducing agent, such as zinc in the presence of a suitable carboxylic acid, such as aqueous acetic acid. Aroylmethoxycarbonylamino can be cleaved also by treatment wiith a nucleophilic, preferably salt-forming reagent, such as sodium thiophenolate, and 4-nitrobenzyloxycarbonylamino can be cleaved also by treatment with an alkali metal dithionite, for example sodium dithionite. Optionally substituted diphenylmethoxycarbonylamino, tert.-lower alkoxycarbonylamino or 2-trisubstituted silylethoxycarbonylamino can be freed by treatment with a suitable acid, for example formic acid or trifluoroacetic acid, optionally substituted benzyloxycarbonylamino can be freed, for example, by means of hydrogenolysis, that is to say by treatment with hydrogen in the presence of a suitable hydrogenation catalyst, such as a palladium catalyst, optionally substituted triarylmethylamino or formylamino can be freed, for example, by treatment with an acid, such as a mineral acid, for example hydrochloric acid, or an organic acid, for example formic acid, acetic acid or trifluoroacetic acid, optionally in the presence of water, and an amino group protected by an organic silyl group can be freed, for example, by means of hydrolysis or alcoholysis. An amino group protected by 2-haloacetyl, for example 2-chloroacetyl, can be freed by treatment with thiourea in the presence of a base, or with a thiolate salt, such as an alkali metal thiolate, of thiourea and subsequent solvolysis, such as alcoholysis or hydrolysis, of the resulting condensation product. An amino group protected by 2-substituted silylethoxycarbonyl can be converted into free amino also by treatment with a salt of hydrofluoric acid that yields fluoride anions, as described above in connection with the freeing of a correspondingly protected carboxy group. Equally silyl, such as trimethylsilyl, that is bonded directly to a hetero atom, such as nitrogen, can be removed by means of fluoride.

Amino protected in the form of an azido group is converted into free amino, for example by reduction, for example by catalytic hydrogenation with hydrogen in the presence of a hydrogenation catalyst, such as platinum oxide, palladium or Raney nickel, or alternatively by treatment with zinc in the presence of an acid, such as acetic acid. Catalytic hydrogenation is carried out preferably in an inert solvent, such as a halogenated hydrocarbon, for example methylene chloride, or alternatively in water or a mixture of water and an organic solvent, such as an alcohol or dioxan, at approximately from 20° to 25° C., or alternatively while cooling or heating.

A hydroxy or mercapto group protected by a suitable acyl group, an organic silyl group or by optionally substituted 1-phenyl-lower alkyl is freed analogously to a correspondingly protected amino group. A hydroxy or mercapto group protected by 2,2-dichloroacetyl is freed, for example, by basic hydrolysis, and a hydroxy or mercapto group etherified by tert.-lower alkyl or by a 2-oxa- or 2-thia-aliphatic or -cyclo-aliphatic hydrocarbon radical is freed by acidolysis, for example by treatment with a mineral acid or a strong carboxylic acid, for example trifluoroacetic acid. Two hydroxy groups that are protected together by means of a preferably substituted methylene group, such as by lower alkylidene, for example isopropylidene, cycloalkylidene, for example cyclohexylidene, or benzylidene, can be freed by acid solvolysis, especially in the presence of a mineral acid or a strong organic acid.

Unless stated otherwise hereinbefore, processes (a) to (k) are carried out in an inert solvent or solvent mixture at a temperature of between approximately −20° and approximately +120° C., and, if necessary, under protective gas.

The starting materials required to carry out processes (a) to (k) described above are known or can be manufactured according to processes known per se, for example according to or analogously to the processes described in this Application.

Salts of compounds of the formula (I) having salt-forming groups can be manufactured in a manner known per se. For example, salts of compounds of the formula (I) having acidic groups can be formed, for example, by treatment with metal compounds, such as alkali metal salts of suitable organic carboxylic acids, for example the sodium salt of α-ethylcaproic acid, or with inorganic alkali metal or alkaline earth metal salts, for example sodium bicarbonate, or with ammonia or a suitable organic amine, preferably stoichiometric amounts or only a small excess of the salt-forming agent being used. Acid addition salts of compounds of the formula (I) having at least one basic group, for example a free amino group, are obtained in customary manner, for example by treatment with an acid or a suitable anion exchange reagent. Internal salts of compounds of the formula (I) that contain, for example, a free carboxy group and a free amino group can be formed, for example, by neutralising salts, such as acid addition salts, to the isoelectric point, for example with weak bases, or by treatment with liquid ion exchangers.

Salts can be converted in customary manner into the free compounds, metal and ammonium salts, for example, by treatment with suitable acids, and acid addition salts, for example, by treatment with a suitable basic agent.

Stereoisomeric mixtures, especially diastereoisomeric mixtures, can be separated into the individual isomers in a manner known per se, for example by fractional crystallisation, chromatography, etc..

Racemates can be split in a manner known per se, for example after converting the optical antipodes into diasteroisomers, for example by reaction with optically active acids or bases.

At individual centres of asymmetry the configuration can deliberately be reversed. For example, the configuration at a carbon atom carrying a hydroxy group can be epimerised by second order nucleophilic substitution after converting the hydroxy group into a good leaving group.

The invention relates also to those forms of the process in which a compound obtainable as an intermediate at any stage of the process is used as starting material and the remaining steps are carried out, or the process is discontinued at any stage, or a compound obtainable according to the process of the invention is produced under the process conditions and is further processed in situ.

The present invention relates also to novel starting materials and/or intermediates and to processes for their manufacture. The starting materials and the reaction conditions are preferably so chosen that the compounds mentioned in this Application as being especially preferred are obtained.

The pharmacologically acceptable compounds of the present invention can be used, for example, for the manufacture of pharmaceutical preparations that contain an effective amount of the active ingredient together or in admixture with a significant amount of inorganic or organic, solid or liquid pharmaceutically acceptable carriers.

The pharmaceutical preparations according to the invention are those for enteral, such as nasal, rectal or oral, administration, and preferably for parenteral, such as intramuscular or intravenous, administration to warm-blooded animals, which contain an effective dose of the pharmacological active ingredient on its own or together with a significant amount of a pharmaceutically acceptable carrier. The dosage of the active ingredient depends on the species, body weight, age and individual condition of the warm-blooded animal, on the disease to be treated and also on the mode of administration.

The dosages to be administered to warm-blooded animals, for example humans, weighing approximately 70 kg are between approximately 3 mg and approximately 3 g, preferably between approximately 10 mg and approximately 1 g, for example approximately 300 mg, per warmblooded animal per day, distributed over preferably from 1 to 3 single doses which may, for example, be of equal size. Children usually receive half the adult dosage.

The novel pharmaceutical preparations contain from approximately 1% to approximately 95%, preferably from approximately 20% to approximately 90%, of active ingredient. Pharmaceutical preparations according to the invention may, for example, be in unit dose form, such as ampoules, phials, suppositories, dragées, tablets or capsules.

The pharmaceutical preparations of the present invention are produced in a manner known per se, for example by means of conventional dissolving, lyophilising, mixing, granulating or confectioning processes.

Preferably, solutions of the active ingredient, or alternatively suspensions, and especially isotonic aqueous solutions or suspensions, are used, it being possible, for example in the case of lyophilised preparations which contain the active ingredient on its own or together with a carrier, for example mannitol, to prepare these before use. The pharmaceutical preparations may be sterilised and/or contain adjuncts, for example preservatives, stabilisers, wetting agents and/or emulsifiers, solubilisers, salts for regulating the osmotic pressure and/or buffers, and are produced in a manner known per se, for example by means of conventional dissolving or lyophilising processes. The solutions or suspensions mentioned may contain substances that increase the viscosity, such as sodium carboxymethylcellulose, carboxymethylcellulose, dextran, polyvinylpyrrolidone or gelatine.

Suspensions in oil contain as oily component the vegetable, synthetic or semi-synthetic oils which are customary for injection purposes. As such there may be mentioned especially liquid fatty acid esters containing as acid component a long-chained fatty acid having from 8 to 22, especially from 12 to 22, carbon atoms, such as, for example, lauric acid, tridecylic acid, myristic acid, pentadecylic acid, palmitic acid, margaric acid, stearic acid, arachidic acid, behenic acid or corresponding unsaturated acids, such as, for example, oleic acid, elaidic acid, erucic acid, brassidic acid or linoleic acid. The alcohol component has a maximum of 6 carbon atoms and is a mono- or polyhydric, for example mono-, di- or tri-hydric alcohol, for example methanol, ethanol, propanol, butanol or pentanol or the isomers thereof, but above all glycol or glycerine. There may be mentioned as fatty acid esters, therefore, for example: ethyl oleate, isopropyl myristate, isopropyl palmitate, "Labrafil M 2735" (polyoxyethylene glycerine trioleate manufactured by Gattefossé, Paris), "Miglyol 812" (triglyceride of saturated fatty acids having the chain length $C_8$ to $C_{12}$ manufactured by Chemische Werke Witten/Ruhr, Germany), but especialy vegetable oils such as cotton seed oil, almond oil, olive oil, castor oil, sesame oil, soya bean oil and, above all, groundnut oil.

The production of injectable preparations is carried out in customary manner under anti-microbial conditions, as is also the filling of ampoules or phials and the closing of the containers.

Pharmaceutical preparations for oral administration can be obtained by combining the active ingredient with solid carriers, optionally granulating a resulting mixture and processing the mixture or granulate, if desired or necessary after the addition of suitable adjuncts, to form tablets or dragée, cores. They can also be incorporated into plastics carriers which release the active ingredients, or allow them to diffuse, in a controlled manner.

Suitable carriers are especially fillers, such as sugars, for example lactose, saccharose, mannitol or sorbitol, cellulose preparations and/or calcium phosphates, for example tricalcium phosphate or calcium hydrogen phosphate, also binders, such as starch pastes using, for example, corn, wheat, rice or potato starch, gelatine, tragacanth, methylcellulose, hydroxypropylmethylcellulose, sodium carboxymethylcellulose and/or polyvinylpyrrolidone, and/or, if desired, disintegrators, such as the above-mentioned starches, also carboxymethyl starch, cross-linked polyvinylpyrrolidone, agar, alginic acid or a salt thereof, such as sodium alginate. Adjuncts are especially flow-regulating agents and lubricants, for example silica, talc, stearic acid or salts thereof, such as magnesium stearate or calcium stearate, and/or polyethylene glycol. Dragée cores are provided with suitable coatings that may be resistant to gastric juices, there being used, inter alia, concentrated sugar solutions which may contain gum arabic, talc, polyvinylpyrrolidone, polyethylene glycol and/or titanium dioxide, lacquer solutions in suitable organic solvents or solvent mixtures or, for the production of coatings that are resistant to gastric juices, solutions of suitable cellulose preparations, such as acetylcellulose phthalate or hydroxypropylmethylcellulose phthalate. Dyes or pigments can be added to the tablets or dragée coatings, for example for identification purposes or to indicate different doses of active ingredient.

The following Examples illustrate the invention. Temperatures are given in degrees Centigrade.

Unless stated otherwise, the $R_f$ values are determined on silica gel thin-layer plates in the following solvent systems:

A: n-BuOH-AcOH-H$_2$O (67:10:23)
B: Ethyl acetate-pyridine-AcOH-H$_2$O (62:21:6:11)
C: n-BuOH-pyridine-AcOH-H$_2$O (38:24:8:30)
D: Pyridine-n-BuOH-n-amyl alcohol-methyl ethyl ketone-AcOH-formic acid-H$_2$O (25:20:15:10:3:3:25)
E: CHCl$_3$-MeOH-H$_2$O-AcOH (70:40:10:0.5)
F: CHCl$_3$-MeOH-H$_2$O-AcOH (90:10:1:0.5)
G: CHCl$_3$-MeOH-H$_2$O-AcOH (75:27:5:0.5)
H: Ethyl acetate-AcOH-H$_2$O-MeOH (67:10:23:12)
I: CHCl$_3$-MeOH-AcOH-H$_2$O (80:20:3:3)
K: n-BuOH-pyridine-formic acid-H$_2$O (42:24:4:20)
L: CHCl$_3$-MeOH-AcOH-H$_2$O (70:30:5:5)
M: n-butanol-pyridine-AcOH-H$_2$O (42:24:4:30)
N: n-butanol-pyridine-formic acid-H$_2$O (44:24:2:20)
O: CHCl$_3$-MeOH-H$_2$O-AcOH (55:47:13:0.5)

For example, hereinafter "$R_f$(A)" denotes that the $R_f$ value was determined in system A. The ratio of the solvents to one another is given in proportions by volume.

Abbreviations

Ac=acetyl
Boc=tert.-butoxycarbonyl
Bu=butyl
DCCI=dicyclohexyl carbodiimide
DCH=dicyclohexylurea
DMF=dimethylformamide Et = ethyl
HOBt = 1-hydroxybenzotriazole
HONB = N-hydroxy-5-norbornene-2,3-dicarboxylic acid imide
H-Sta(Me)-OH = O-methyl-statin = (4S)-amino-(3S)-ethoxy-6-methylheptanecarboxylic acid
H-Sta(Ac)-OH = O-acetyl-statin = (3S)-acetoxy-(4S)-amino-6-methylheptanecarboxylic acid
Lac = -O-CH(CH$_3$)-CO- (bivalent radical of lactic acid H-Lac-OH), unless stated otherwise having the L-configuration
Me = methyl
m.p. = melting point
Su = succinimidyl
TFA = trifluoracetic acid
vol. = parts by volume
Z = benzyloxycarbonyl
$\phi$ = diameter Thin layer chromatography is on silica gel unless stated otherwise.

EXAMPLE 1

540 mg of H- Pro-His-Pro-Phe-His-Sta-Val-Tyr-Lys-Ome ×4 TFA are dissolved in 9 ml of H$_2$O (pH = 1.85) and the pH value is adjusted to 5.0 with 0.3N NH$_3$. 55 µl of 0.5% aqueous trypsin solution are added and the whole is stirred at room temperature, the pH value being maintained at 5.0 by the addition of 0.3N NH$_3$ by means of pH stat. When the absorption of the base is complete (approximately 1 hour), 0.5 ml of glacial acetic acid is added and the whole is heated for 2 minutes at 95° and lyophilised. For conversion into the acetate, the whole is dissolved in 0.05N AcOH and filtered slowly through a column ($\phi$ = 1 cm, length = 12 cm) of weakly basic ion exchanger (for example Merck No. II) in the acetate form, the eluate is concentrated and lyophilised again. H-Pro-His-Pro-Phe-His-Sta-Val-Tyr-Lys-OH×AcOH is obtained in the form of amorphous, readily water-soluble powder; R$_f$(C) = 0.28; R$_f$(D) = 0.17; R$_f$(K) = 0.20.

The starting material H-Pro-His-Pro-Phe-His-Sta-Val-Tyr-Lys-OMe×4 TFA is obtained as follows:

Stage 1.1: 14.5 g of Z-Lys(Boc)-OMe-[A. Costopanagiotis e-t al., J. Org. Chem., 33, 1261-1 (1968)] are dissolved in 145 ml of 95% strength MeOH and, after the addition of 1 g of pd-on-carbon (10% pd), hydrogenated with CO$_2$-absorption until saturation. The catalyst is filtered off, the filtrate is concentrated to an oil, 30 ml of DMF are added and the whole is concentrated again. This solution, which contains H-Lys(Boc)-OMe, is further used directly.

Stage 1.2: 13.8 g of Z-Val-Tyr-OH [R. Schwyzer et al., Helv. Chim. acta. 41, 1273 (1958)] and 5.1 g of HOBt×H$_2$O are dissolved in 100 ml of DMF and there is added thereto the above solution of H-Lys(Boc)-OMe in a small amount of DMF. The whole is cooled to 0°, 7.6 g of DCCI are added and the whole is stirred for 6 hours at 0° and for 10 hours at room temperature. The DCH which has separated out is filtered off and the filtrate is concentrated to dryness. Purification is carried out by triturating with diisopropyl ether and by dissolving and reprecipitating from trifluoroethanol/ethyl acetate/petroleum ether, yielding Z-Val-Tyr-Lys(Boc)-OMe; R$_f$(F) = 0.39.

Stage 1.3: 8 g of Z-Val-Iyr-Lys(Boc)-OMe are suspended in 160 ml of 95% strength MeOH and, after the addition of 800 mg of Pd-on-carbon, hydrogenated with CO$_2$-absorption, the substance dissolving. When H$_2$-absorption is complete filtration is carried out, and the filtrate is concentrated to dryness and recrystallised in the form of needles from MeOH-H$_2$, yielding H-Val-Tyr-Lys(Boo)-OMe: m.p. = 165°-166°; R$_f$(G) = 0.54; R$_f$(I) = 0.29.

Stage 1.4: 1 g of Z-Sta-OH (for manufacture see stage 1.12), 1.49 g of U-Val-Tyr-Lys(Boc)-OMe and 650 mg of HOBt×H$_2$O are dissolved in 15 ml of DMF, 704 mg of DCCI are added and the whole is stirred for 20 hours at room temperature. The DCH whioh has crystallised out is filtered off at 0°, the filtrate is concentrated until it is of an oily nature, and after the addition of 30 ml of diisopropyl ether the condensation product is precipitated in the form of a powder and, after stirring for 10 minutes at 0°, filtered off. It is purified by Craig partitioning in the system hexane/isopropanol/0.1N acetic acid (10:10:3) over 900 stages, K-value (distribution coefficient) = 0.29, yielding Z-Sta-Val-Iyr-Lys(Boc)-OMe; R$_f$(F) = 0.31.

Stage 1.5: 850 mg of Z-Sta-Val-Tyr-Lys(Boc)-OMe are dissolved in 17 ml of 95% strength MeOH and hydrogenated with 85 mg of Pd-on-carbon with CO$_2$-absorption until saturation (approximately 1 hour). The catalyst is filtered off, the filtrate is concentrated to dryness and dried in a high vacuum at 40° yielding H-Sta-Val-Tyr-Lys(Boc)-OMe in the form of an amorphous powder; R$_f$(E) = 0.58; R$_f$(H) = 0.50. The resulting product is further reacted in stage 1.10.

Stage 1.6: 7 g of Z-Pro-Phe-His-OMe [H. Dewald et al., J. Med. Pharm. Chem. 7, 50 (1964)] are suspended in 200 ml of 95% strength MeOH, 0.7 g of Pd-on-carbon is added and hydrogenation with CO$_2$-absorption is carried out until saturation. The catalyst is filtered off, the filtrate is concentrated to dryness, the amorphous foamy residue is pulverised and dried in a high vacuum at 40° yeilding H-Pro-Phe-His-OMe; R$_f$(E) = 0.21.

Stage 1.7: 1.25 g of Boc-Pro-OSu [G. W. Anderson et al., J. Amer. Chem. Soc. 86, 1839 (1964)] and 0.68 g of H-His-OH are suspended in 4 ml of H$_2$O and 2 ml of dioxan. While stirring vigorously, 2N NaOH is added by means of a pH stat at a pH value of 9.0. After 45 minutes the absorption of NaOH ceases. The now clear solution is stirred for a further 10 minutes, the pH value is adjusted subsequently to 5.0 with 4N HCl, and the whole is concentrated to approximately 5 ml. After the addition of 20 ml of H$_2$O, the whole is again concentrated to approximately 5 ml and then purified by chromatography over a column of absorber resin, diaion HP-20 ($\phi$ = 1.6 cm; length = 20 cm). The bulk of this product is eluted with 20% isopropanol in H$_2$O. The fractions that are pure according to thin layer chromatography are combined, concentrated almost to dryness and, after the addition of H$_2$O, lyophilised, yielding Boc-Pro-His-OH in the form of an amorphous powder; R$_f$(E) = 0.45; R$_f$(A) = 0.21.

Stage 1.8: 6.59 g of Boc-Pro-His OH, 7 g of H-Pro-Phe-His-OMe (from stage 1.6) and 5.65 g of HONB are dissolved in 35 ml of DMF. After cooling the solution to 0°, 4.82 g of DCCI are added and the whole is stirred for 6 hours in an ice bath and overnight at room temperature. After stirring for a further 30 minutes at 0°, DCH is filtered off, the filtrate is concentrated to dryness and, by means of the addition of 200 ml of diisopropyl ether, is precipitated in the form of a glutinous mass, and dried. It is then dissolved in 188 ml of MeOH, 6 ml of glacial acetic acid and 6 ml of H$_2$O, heated for 1 hour at 60°, concentrated to 40 ml and precipitated again with 400 ml of diisopropyl ether in the form of an oil. After 1 hour at 0°, the supernatant solution is decanted off and the residue is dried, yielding Boc-Pro-His-Pro-Phe-His-OMe; $R_f(A)=0.17$; $R_f(E)=0.51$.

Stage 1.9: 17.2 g of crude Boc-Pro-His-Pro-Phe-His-OMe are dissolved in 54 ml of MeOH, 650 ml of 0.1N NaOH are added, the whole is left to stand for 15 minutes at 25°, neutralised by the addition of 650 ml of 0.1N HCl concentratod to dryness. The residue is dissolved in 120 ml of $H_2O$, the pH value is adjusted exactly to 6.8 and this solution is subjected in the system n-butanol/-$H_2O$ to Craig partitioning over 500 stages; (K=2.8). The fractions that are pure according to thin layer chromagotraphy analysis are combined, concentrated to dryness, dissolved in $H_2O$ and lyophilised, yielding Boc-Pro-His-Pro-Phe-His-OH in amorphous form; $R_f$ (A)=0,15; $R_f(C)=0.42$; $R_f(E)=0.25$.

Stage 1.10: 840 mg of Boc-Pro-His-Pro-Phe-His-OH, 600 mg of H-Sta-Val-Tyr-Lys(Boc)-OMe (from stage 1.5) and 250 mg of HONB are dissolved in 6 ml of DMF, cooled to 0°, and 290 mg of DCCI are added. The whole is stirred for 6 hours at 0° and for 24 hours at 25° the DCH is filtered off, and the filtrate is concentrated to dryness by evaporation. The residue is dissolved in 18.8 ml of MeOH, 0.6 ml of glacial acetic acid and 0.6 ml of $H_2O$, heated for 1 hour at 60°, concentrated to approximately 3 ml, and the peptide is precipitated in the form of greasy material with 20 ml of diisopropyl ether. It is purified by Craig partitioning in the system MeOH/0.1N AcOH/ethylene chloride/-chloroform (10:3:8:4) over 750 stages; K=0.75. The chromatographically pure middle fraction is isolated by strong concentration and lyophilisation, yielding Boc-Pro-His-Pro-Phe-His-Sta-Val-Tyr-Lys(Boc)-OMe in the form of an amorphous powder; $R_{fn}(B)=0.38$; $R_f$(I)=0.46; $R_f(C)=0.64$.

Stage 1.11: 470 mg of Boc-Pro-His-Pro-Phe-His-Sta-Val-Tyr-Lys(Boc)-OMe are dissolved at 25° in 2.3 ml of 95% strength TFA and the whole is left to stand for 30 minutes. The H-Pro-His-Pro-Phe-His-Sta-Val-Tyr-Lys-OMe formed is precipitated at 0° in pulverulent form as the trifluoroacetate by the addition of 20 ml of diisopropyl ether, is filtered off and dried; $R_f$ (C)=0.36; $R_f$ (D)=0.24.

Stage 1.12: The Z-Sta-OH used in stage 1.4 is obtained in the following manner: 6.0 g of (3S,4S)-N-Z-statin ethyl ester are taken up in 220 ml of dioxan and 220 ml of water. The turbid solution is adjusted to a pH value of 11.90 at 0° with 1N NaOH. The mixture is then stirred for 30 minutes at 0°, the pH value rising to 12.14. The clear reaction solution is adjusted at 0° with 1N HCl to a pH value of 6.5, the dioxan is evaporated off in vacuo, and the residue is extracted by shaking between ether and saturated sodium bicarbonate solution. The aqueous phase is adjusted to a pH value of 2.5 with 10% strength citric acid and extracted with ether. The organic phase is washed with brine and dried. Crystallisation of the residue from ether/petroleum ether (1:1) yields (3S,4S)-N-Z-statin [Z-Sta-OH, (4S)-benzyloxycarbonylamino-(3S)-hydroxy-6-methylheptanecarboxylic acid in the form of white crystals, m.p. 116°-117°, $[\alpha]_D^{20}=-33°$ ($CH_3OH$, c=1.23)]. Starting from (3R,4S)-N-Z-statin ethyl ester there is obtained in an analogous manner 3R,4S-N-Z-statin [white crystals, m.p. 135°-136°, $[\alpha]_D^{20}=-21°$ ($CH_3OH$, c=1.13)].

Stage 1.13: The starting material used in stage 1.12 is obtained in the following manner: At −20° under argon, 136.9 ml (0.233 mole) of a 1.7 molar solution of butyllithium in hexane are added dropwise to a solution of 33 ml (0.233 mole) of diisopropylamine in 75 ml of tetrahydrofuran. After 15 minutes the whole is cooled to −76°, 22.78 ml (0.233 mole) of ethyl acetate are added dropwise and stirring is carried out for 15 minutes. In the course of 20 minutes there is then added dropwise thereto a solution, precooled to −76°, of 34.1 g (0.137 mole) of N-Z-leucinal [(2S)-benzyloxycarbonylamino-4-methylpentanal; Ito et al., Chem. Pharm. Bull. 23, 3081 (1975)] in 100 ml of tetrahydrofuran. The reaction mixture is then stirred for 15 minutes at −76° and subsequently 118 ml of 2N HCl are added in the course of 30 minutes. This suspension is adjusted at 0° with 2N HCl to a pH value of 2.5, after heating to room temperature extracted with ether, and the organic phase is washed with brine (saturated sodium chloride solution) and dried. The crude product is separated by means of medium pressure chromatography [LiChroprep Si 60, 25–40 μm, ethyl acetate/hexane (1:5)]. There are obtained by elution first (3S,4S)-N-Z-statin ethyl ester [wax-like crystals, m.p. 51°-54°, $[\alpha]_D^{20}=-26°$ ($CH_3OH$, c=0.69)] and then the more polar (3R,4S)-N-Z-statin ethyl ester [white crystals, m.p. 103°-104°, $[\alpha]_D^{20}=-17°$ ($CH_3OH$, c=1.00)].

EXAMPLE 2

370 mg of H-Pro-His-Pro-Phe-His-Sta-Ile-His-Lys-OMe×5 TFA are dissolved in 8 ml of $H_2O$. The pH value is increased to 5.0 with 0.3N $NH_3$, whereupon 40 μl of a 1% aqueous solution of trypsin are added and the pH value is maintained constant by means of a pH stat with the addition of 0.3N $NH_3$. The absorption of base is complete after approximately 40 minutes. 1 ml of glacial acetic acid is added, the whole is heated for 2 minutes in a boiling water bath, concentrated to approximately 3 ml and lyophilised. The residue is dissolved in 3 ml of 0.05N AcOH, converted into the acetate by slowly being filtered through a column (φ=1 cm, length=10 cm) of weakly basic ion exchanger (Merck No. II) in acetate form, and the eluate is again lyophilised, yielding H-Pro-His-Pro-Phe-His-Sta-Ile-His-Lys-OH×AcOH in the form of amorphous white powder; $R_f(D)=0.12$; $R_f(K)=0.14$.

The starting material H-Pro-His-Pro-Phe-His-Sta-Ile-His-Lys-OMe×5 TFA can be obtained in the following manner:

Stage 2.1: 1.6 g of Z-His-Lys(Boc)-OMe [S. Guttman et al., Helv. Chim. Acta 52, 1789 (1969)] are dissolved in 33 ml of MeOH, 3 ml of 1N HCl and 160 mg of Pd-on-carbon (10% pd) are added thereto, and hydrogenation is carried out with $CO_2$-absorption until saturation. After filtering off the catalyst, the whole is concentrated, the oily residue is dissolved in 20 ml of DMF and again concentrated to approximately 10 ml, yielding H-His-Lys(Boc)-OMe in the form of a solution which is immediately further processed in stage 2.2.

Stage 2.2: 1.32 g of Z-Ile-OSu [G. W. Anderson et. al., J. Amer. Chem. Soc. 86, 1839 (1964)] are dissolved in the above solution of H-His-Lys(Boc)-OMe in approximately 10 ml of DMF and mixed with 0.41 ml of $NEt_3$. The whole is left to stand for 8 hours at room temperature, 15 ml of diisopropyl ether are added, and the whole is homogenised and filtered. The residue obtained by filtering with suction is dissolved in 15 ml of methanol and added at 0° to 23 ml of aqueous $NaHCO_3$ solution. The resulting precipitate is filtered off, washed with $H_2O$, dried and dissolved and reprecipitated from MeOH/ethyl acetate/petroleum ether, yielding Z-Ile-His-Lys(Boc)-OMe in the form of amorphous powder; $R_f(B)=0.65$; $R_f(I)=0.48$.

Stage 2.3: 8 g of Z-Ile-His-Lys(Boc)-OMe are suspended in a mixture of 80 ml of MeOH, 8 ml of $H_2O$ and 80 ml of trifluoroethanol, and hydrogenated with 800 mg of Pd-on-carbon (10% Pd) with $CO_2$-absorption until saturation, the initially undissolved material being dissolved. The catalyst is filtered off, the filtrate is concentrated to dryness and the resinous residue is crystallised from acetonitrile, yielding H-Ile-His-Lys(Boc)-OMe in the form of needles having a melting point of 129°-130°; $R_f(I)=0.12$; $R_f(B)=0.14$.

Stage 2.4: 900 mg of Z-Sta-OH (for manufacture see stage 1.12), 1.24 g of H-Ile-His-Lys(Boc)-OMe and 560 mg of HOBt×$H_2O$ are dissolved in 13 ml of DMF. After the addition of 600 mg of DCCI, the whole is left to stand at room temperature for 20 hours, then the DCH which has crystallised out is filtered off and the filtrate is concentrated to dryness. The greasy residue is triturated at 0° with 30 ml of diisopropyl ether, the solvent is decanted and the residue is dried. Purification is carried out by Craig partitioning in the system methanol/buffer/ethylene chloride/chloroform (10:3:8:4; buffer=14.3 ml of glacial acetic acid and 9.6 g of ammonium acetate in 1000 ml of $H_2O$) over 700 stages. The thin layer chromatographically pure fractions (K=0.5) are combined, strongly concentrated and lyophilised. To remove acetic acid, the product is dissolved and reprecipitated from 5% strength methanolic $NaHCO_3$ solution, yielding Z-Sta-Ile-His-Lys(Boc)-OMe in the form of amorphous powder; $R_f(B)=0.8$; $R_f(I)=0.56$.

Stage 2.5: 1 g of Z-Sta-Ile-His-Lys(Boc)-OMe is dissolved in 10 ml of 95% strength MeOH and hydrogenated with 100 mg of Pd-on-carbon (10% pd) with $CO_2$-absorption until saturation. After filtering off the catalyst and concentrating to dryness there is obtained H-Sta-Ile-His-Lys(Boc)-OMe in the form of amorphous powder, which is directly further processed; $R_f(B)=0.32$; $R_f(I)=0.17$.

Stage 2.6: 480 mg of Boc-Pro-His-Pro-Phe-His-OH (for manufacture see Example 1, stage 1.9), 340 mg of H-Sta-Ile-His-Lys(Boc)-OMe and 150 mg of HONB are dissolved, while heating, in 3.5 ml of DMF. After cooling to 0°, 170 mg of DCCI are added, whereupon stirring is carried out for 5 hours at 0° and the whole is left to stand at room temperature for 20 hours. The condensation product is precipitated by the addition of 35 ml of diisopropyl ether and filtered off. It is purified by Craig partitioning over 1000 stages in the same solvent system as described in stage 2.4 (K=0.6), yielding Boc-Pro-His-Pro-Phe-His-Sta-Ile-His-Lys(Boc)-OMe; $R_f$(A)=0.22; $R_f(B)=0.21$; $R_f(E)=0.54$.

Stage 2.7 330 mg of Boc-Pro-His-Pro-Phe-His-Sta-Ile-His-Lys(Boc)-OMe are dissolved in 1.7 ml of 95% strength trifluoroacetic acid and left to stand for 30 minutes at 25°. Then, 14 ml of diisopropyl ether are added, the whole is stirred for 30 minutes at 0°, filtered and dried in a high vacuum over KOH, yielding H-Pro-His-Pro-Phe-His-Sta-Ile-His-Lys-OMe×5 TFA; $R_f$(D)=0.17; $R_f(K)=0.20$.

EXAMPLE 3

The following are obtained in a manner analogous to the processes described in this Application:
H-Pro-His-Pro-Phe-His-Sta-$NH_2$,

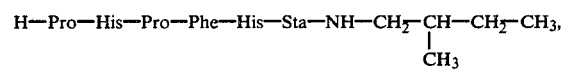

H-Pro-His-Pro-Phe-His-Sta-OH,
H-Pro-His-Pro-Phe-His-(3R,4S)-Sta-Val-Tyr-Lys-OH,
H-Pro-His-Pro-Phe-His-Sta(Me)-Ile-His-Lys-OH,
H-Pro-His-Pro-Phe-His-Sta(Ac)-Ile-His-Lys-OH,

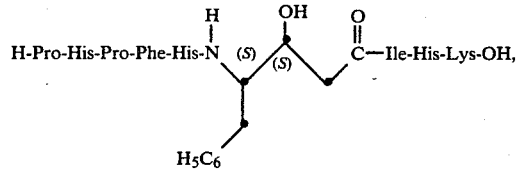

H-Pro-Phe-His-Sta-Ile-His-Lys-OH,
H-Pro-His-Pro-Phe-His-Sta-$OC_2H_5$,
H-Pro-His-Pro-Phe-His-(3R,4S)-Sta-Ile-His-Lys-OH,
H-Pro-His-Pro-Phe-His-Sta(Me)-Val-Tyr-Lys-OH,
H-Pro-His-Pro-Phe-His-Sta(Ac)-Val-Tyr-Lys-OH,

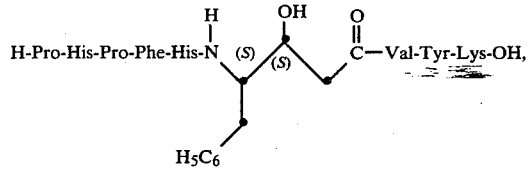

H-Pro-His-Pro-Phe-His-Sta-Val-Tyr-$NH_2$,
H-Pro-His-Pro-Phe-His-Sta-Ile-His-$NH_2$,
H-Pro-His-Pro-Phe-His-Sta-Ile-D-His-$NH_2$,

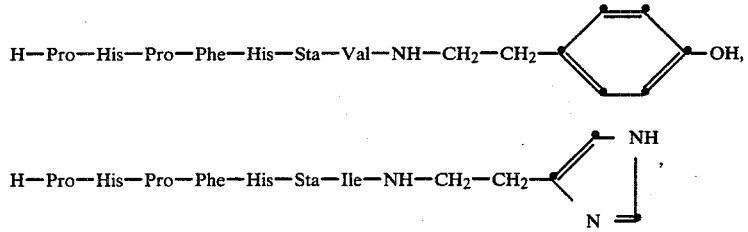

H-Pro-His-Pro-Phe-His-Sta-Phe-Val-Tyr-Lys-OH,
H-His-Pro-Phe-His-Sta-Ile-His-Lys-OH,
H-D-His-Pro-Phe-His-Sta-Ile-His-Lys-OH,
H-Arg-Arg-Pro-Phe-His-Sta-Ile-His-Lys-OH and
H-Arg-D-Arg-Pro-Phe-His-Sta-Ile-His-Lys-OH.

EXAMPLE 4

595 mg of Z-Arg-Arg-Pro-Phe-His-OH (in the form of the trihydrochloride, containing 24% by weight of NaCl), 250 ml of H-Sta-Ile-His-Lys(Boc)-OMe (stage 2.5) and 74 mg of HOBt×$H_2O$ are dissolved or suspended in 2.5 ml of DMF, cooled to 0°, and 110 mg of DCCI are added. The whole is stirred for 10 hours at 0°, left to stand for a further day at room temperature, and NaCl and DCH are filtered off. The filtrate is concentrated to the oil, and the condensation product is precipitated from this by the addition of 50 ml of diisopropyl ether and dried. It is heated for 1 hour at 60° in 8 ml of methanol/glacial acetic acid/$H_2O$ (94:3:3), precipitated at 0° by the addition of 80 ml of diisopropyl ether, filtered and dried. The residue is dissolved in 20 ml of 0.1N acetic acid, the small amount of insoluble material is filtered off, and the filtrate is allowed to run slowly through a column ($\phi=1.2$ cm, length=15 cm) of weakly basic ion exchanger (for example Merck No. II) in acetate form. The eluate is concentrated to 10–15 ml and lyophilised. For purification, it is subjected to Craig partitioning in the system n-butanol/glacial acetic acid/$H_2O$ (4:1:5) over 400 stages; K-value approximately 0.5. The chromatographically pure fractions are combined, concentrated to the oil, dissolved in water and lyophilised, yielding Z-Arg-Arg-Pro-Phe-His-Sta-Ile-His-Lys(Boc)-OMe in the form of amorphous powder (acetate form); $R_f$ (M)=0.55; $R_f$ (N)=0.35; $R_f$ (O)=0.5; $R_f$(L)=0.2.

The starting material Z-Arg-Arg-Pro-Phe-His-OH can be obtained in the following manner:

Stage 4.1: 486 mg of Z-Arg-OH are suspended in 5 ml of DMF and dissolved by the addition of 315 μl of a 5N solution of HCl in dioxan. 500 mg of H-Pro-Phe-His-OMe (stage 1.6) and 185 mg of HOBt×$H_2O$ in solid form are added, a clear solution forming. After cooling to 0°, 325 mg of DCCI are added and the whole is left to stand for 10 hours in an ice bath and for 1 day at room temperature. The precipitated DCH is filtered off, the filtrate is concentrated to 2–3 ml and, from this, the crude product is precipitated by the addition of diisopropyl ether. The crude product is dissolved in 14 ml of methanol/glacial acetic acid/$H_2O$ (94:3:3), heated for 1 hour at 60°, concentrated again to 2–3 ml and precipitated with diisopropyl ether. The precipitate is dissolved in 10 ml of $H_2O$, adjusted to a pH value of 3.0 with 2N HCl and purified by means of Craig partitioning in the system n-butanol/$H_2O$. By concentrating the pure fractions and lyophilising, Z-Arg-Pro-Phe-His-OMe is obtained in the form of the dihydrochloride; $R_f$ (E)=0.45; $R_f$(C)=0.55.

Stage 4.2: 2.5 g of Z-Arg-Pro-Phe-His-OMe are dissolved in 25 ml of 95% strength methanol and, after the addition of 250 mg of Pd-on-carbon, hydrogenated with $CO_2$-absorption until saturation. The catalyst is filtered off and the filtrate is concentrated to dryness, yielding H-Arg-Pro-Phe-His-OMe in the form of an amorphous powder; $R_f$(E)=0.05; $R_f$(C)=0.3.

Stage 4.3: 1.27 g of Z-Arg-OH are dissolved in 20 ml of DMF and 240 μl of a 5N solution of HCl in dioxan while heating gently. After the addition of 1.9 g of H-Arg-Pro-Phe-His-OMe (in the form of the dihydrochloride) and 0.45 g of HOBt×$H_2O$, the whole is cooled to 0° and then 0.85 g of DCCI in solid form is added. After the latter has dissolved, the whole is left to stand for 8 hours in an ice bath and for 1 day at room temperature and the precipitated DCH is filtered off. The filtrate is concentrated to approximately 5 ml and, from this, the peptide is precipitated by the addition of 50 ml of diisopropyl ether and dried. It is dissolved in 45 ml of methanol/glacial acetic acid/$H_2O$ (94:3:3), heated for 1 hour at 60°, again concentrated to approximately 5 ml and precipitated with diisopropyl ether and dried. The crude product is purified by chromatography over 120 g of silica gel (60, Merck, 230–400 mesh) using as eluant chloroform/methanol/$H_2O$/glacial acetic acid (140:80:20:1). The pure fractions are combined, concentrated almost to dryness, dissolved in $H_2O$ and lyophilised, yielding Z-Arg-Arg-Pro-Phe-His-OMe in the form of the dihydrochloride-monoacetate; $R_f$(C)=0.4; $R_f$(E)=0.3.

Stage 4.4: 1.3 g of Z-Arg-Arg-Pro-Phe-His-OMe are dissolved in 26 ml of $H_2O$, left to stand for 5 minutes at 25° after the addition of 6.5 ml of 1N NaOH, and then adjusted to a pH value of 2.5 with 2N HCl and lyophilised. The dry residue is dissolved in 30 ml of $H_2O$ and lyophilised again, whereupon it weighs 1.6 g and contains 0.38 g of NaCl. The resulting Z-Arg-Arg-Pro-Phe-His-OH is in the form of the trihydrochloride and is used in this form for condensation with H-Sta-Ile-His-Lys(Boc)-OMe (stage 2.5); $R_f$(C)=0.3.

EXAMPLE 5

100 mg of Z-Arg-Arg-Pro-Phe-His-Sta-Ile-His-Lys(Boc)-OMe (Example 4) are dissolved in 500 μl of 95% strength TFA, the whole is left to stand for 25 minutes, and precipitation is effected by the addition of 5 ml of diisopropyl ether. The precipitate is filtered off, dried, dissolved in 2 ml of $H_2O$ and, in order to be converted into the acetate, filtered slowly through a column ($\phi=1$ cm, length=8 cm) of weakly basic ion exchanger in acetate form. The eluate is concentrated and lyophilised, yielding Z-Arg-Arg-Pro-Phe-His-Sta-Ile-His-Lys-OMe; $R_f$(D)=0.35; $R_f$(M)=0.3; $R_f$(N)=0.3.

EXAMPLE 6:

145 mg of Z-Arg-Arg-Pro-Phe-His-Sta-Ile-His-Lys(Boc)-OMe (Example 4) are dissolved in 2.5 ml of 95% strength MeOH and, after the addition of 15 mg of Pd-on-carbon, hydrogenated by passing hydrogen through and stirring with a small magnetic rod until the starting material has disappeared completely (according to thin layer chromatography monitoring). The whole is filtered, the filtrate is concentrated to dryness, dissolved in 3 ml of $H_2O$ and lyophilised, yielding H-Arg-Arg-Pro-Phe-His-Sta-Ile-His-Lys(Boc)-OMe; $R_f$(D)=0.32; $R_f$(M)=0.25; $R_f$(N)=0.3.

EXAMPLE 7

200 mg of H-Arg-Arg-Pro-Phe-His-Sta-Ile-His-Lys(Boc)-OMe (Example 6) are dissolved in 1 ml of 95% strength TFA, left to stand for 25 minutes and then precipitation is effected by the addition of 10 ml of diisopropyl ether. The precipitate is filtered off, dried, dissolved in 4 ml of $H_2O$ and, in order to be converted into the acetate, the solution is slowly filtered through a column ($\phi=1$ cm, length=12 cm) of weakly basic ion exchanger in acetate form. The eluate is concentrated to a small volume and lyophilised, yielding H-Arg-Arg-Pro-Phe-His-Sta-Ile-His-Lys-OMe; $R_f$ (D)=0.15; $R_f$ (M)=0.12; $R_f$(N)=0.09.

EXAMPLE 8

80 mg of H-Arg-Arg-Pro-Phe-His-Sta-Ile-His-Lys-OMe (Example 7) are dissolved in 1.5 ml of $H_2O$ and the pH value is adjusted to 5.5 by the addition of 0.1N $NH_3$. 8 μl of a 1% aqueous trypsin solution are added and the pH value is maintained at 5.5 by the addition of 0.1N $NH_3$ by means of a pH stat. After approximately 20 minutes the absorption of base is complete, whereupon 350 μl of glacial acetic acid are added and the whole is heated for 2 minutes in a boiling water bath. The solution is concentrated to dryness, the residue is dissolved in 2 ml of 0.05N AcOH and, in order to separate off the inactivated enzyme, pumped through a column (φ=1.2 cm, length=25 cm) of Biogel P-10 polyacrylamide gel, exclusion limit at a molecular weight of 20 000; manufacturer: Bio-Rad, Richmond, Calif., USA). The fraction having a molecular weight matching the peptide mentioned below, which is ascertained by UV detection, is concentrated to a small volume and lyophilised, yielding H-Arg-Arg-Pro-Phe-His-Sta-Ile-His-Lys-OH; $R_f$ (D)=0.12; $R_f$ (M)=0.07; $R_f$ (N)=0.05.

EXAMPLE 9

The following are obtained in a manner analogous to the processes described in this Application:
H-Pro-Phe-His-Sta-Ala-Sta-OH,
H-Pro-Phe-His-Sta-Ala-Sta-OMe,
H-Pro-Phe-His-Sta-Ala-Sta-NH₂,
Z-Pro-Phe-His-Sta-Ala-Sta-OH,
Z-Pro-Phe-His-Sta-Ala-Sta-OMe,
Z-Pro-Phe-His-Sta-Ala-Sta-NH₂,
Boc-Pro-Phe-His-Sta-Ala-Sta-OH,
Boc-Pro-Phe-His-Sta-Ala-Sta-OMe,
Boc-Pro-Phe-His-Sta-Ala-Sta-NH₂,
H-Pro-Phe-His-Sta-Ile-Sta-OH,
H-Pro-Phe-His-Sta-Ile-Sta-OMe,
H-Pro-Phe-His-Sta-Ile-Sta-NH₂,
Z-Pro-Phe-His-Sta-Ile-Sta-OH,
Z-Pro-Phe-His-Sta-Ile-Sta-OMe,
Z-Pro-Phe-His-Sta-Ile-Sta-NH₂,
Boc-Pro-Phe-His-Sta-Ile-Sta-OH,
Boc-Pro-Phe-His-Sta-Ile-Sta-OMe,
Boc-Pro-Phe-His-Sta-Ile-Sta-NH₂,
(Boc, Z or H)-Pro-Phe-His-Sta-Gly-Sta-(OH, OMe or NH₂),
(Boc, Z or H)-Pro-Phe-His-Sta-Sar-Sta-(OH, OMe or NH₂),

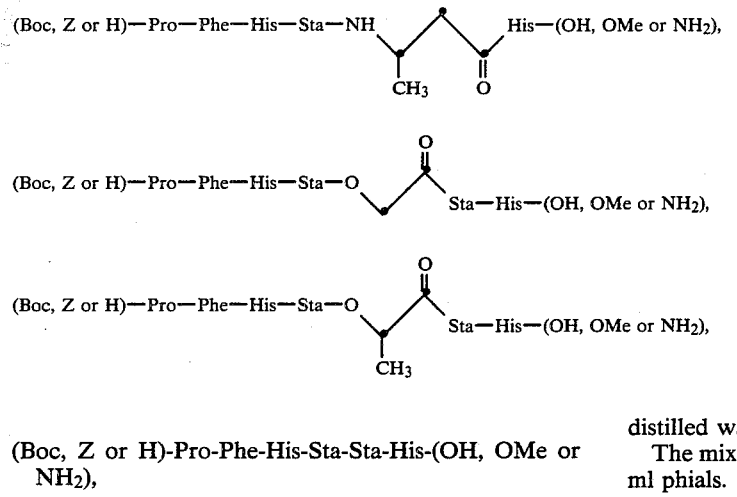

(Boc, Z or H)-Pro-Phe-His-Sta-Sta-His-(OH, OMe or NH₂),

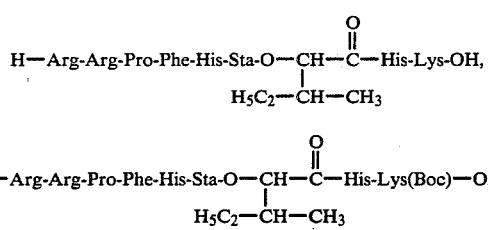

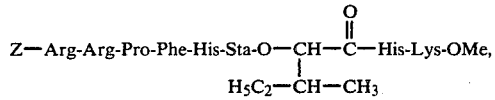

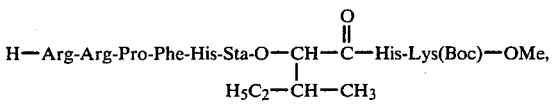

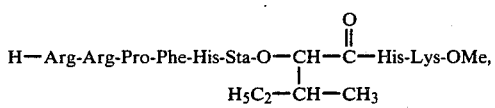

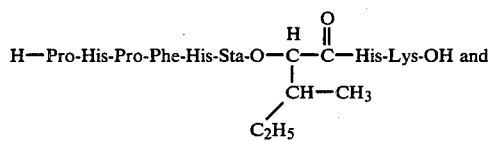

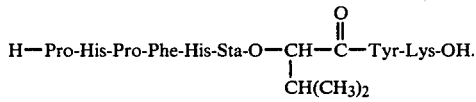

EXAMPLE 10

Gelatine solution

A sterile-filtered aqueous solution of H-Arg-Arg-Pro-Phe-His-Sta-Ile-His-Lys-OH is mixed under aseptic conditions, while heating, with a sterile gelatine solution that contains phenol as preservative, so that 1.0 ml of solution has the following composition:
H-Arg-Arg-Pro-Phe-His-Sta-Ile-His-Lys-OH: 1 mg
gelatine: 150.0 mg
phenol: 4.7 mg
distilled water to make up to: 1.0 ml The mixture is filled under aseptic conditions into 1.0 ml phials.

EXAMPLE 11

Sterile dry substance for injection 5 mg of H-Arg-Arg-Pro-Phe-His-Sta-Ile-His-Lys-OH are dissolved in 1 ml of an aqueous solution with 20 mg of mannitol. The solution is sterile-filtered and filled under aseptic conditions into a 2 ml ampoule, deep-frozen and lyophilised. Before being used, the lyophilisate is dissolved in 1 ml of distilled water or 1 ml of physiological salt solution. The solution is used intramuscu-

EXAMPLE 12

Nasal Spray 500 mg of finely ground (<5.0 μ) H-Arg-Arg-Pro-Phe-His-Sta-Ile-His-Lys-OH are suspended in a mixture of 3.5 ml of "Miglyol 812" and 0.08 g of benzyl alcohol. This suspension is introduced into a container with a dosing valve. 5.0 mg of "Freon 12" are then introduced under pressure through the valve into the container. By shaking, the "Freon" is dissolved in the Miglyol-benzyl alcohol mixture. This spray container contains approximately 100 single doses, which can be administered individually.

EXAMPLE 13

A solution of 214 mg of Z-Pro-Phe-His-OH, 152 mg of H-Sta-Ala-Sta-OMe and 56 mg of HOBt×H$_2$O in 6 ml of DMF is stirred in an ice bath and 97 mg of DCCI are added. The whole is stirred for 1 hour at 0° and for 16 hours at 25°, the dicyclohexyl urea formed is filtered off and the filtrate is concentrated by evaporation in a high vacuum. The residue is taken up in 10 ml of a mixture of methanol/glacial acetic acid/water (94:3:3) and stirred for 60 minutes at 60°. The solvent is then removed in a rotary evaporator, the residue is stirred at 0° with a small amount of ethyl acetate, the resulting suspension is filtered, and the filtrate is freed of solvent. After dissolving again in ethyl acetate, extraction is carried out with saturated sodium bicarbonate solution and with sodium chloride solution, and the organic phases are dried and concentrated by evaporation. The residue is chromatographed over 80 g of silica gel (grain size 0.04–0.063 mm) using chloroform/methanol (9:1) as eluant (fractions of approximately 20 ml). Fractions 16–23 are combined, freed of solvent, the residue is taken up in a small amount of methanol, filtered and the filtrate is again concentrated by evaporation. After drying the residue is a high vacuum, Z-Pro-Phe-His-Sta-Ala-Sta-OMe (cf. Example 9) is obtained in the form of a yellowish powder; R$_f$ (G)=0.72; R$_f$ (CHCl$_3$/MeOH [9:1])=0.26

The starting material H-Sta-Ala-Sta-OMe can be obtained as follows:

Stage 13.1: 371 mg of Z-Sta-OH (cf. stage 1.12), 240 mg of H-Ala-OC(CH$_3$)$_3$ and 184 mg of HOBt×H$_2$O are dissolved in 10 ml of DMF. After cooling the solution to 0°, 133 mg of N-methylmorpholine and 321 mg of DCCI are added. The whole is stirred for 1 hour at 0° and for 14 hours at 25°, then the DCH formed is filtered off and the filtrate is concentrated to dryness by evaporation. The residue is taken up in ethyl acetate and the solution is extracted with saturated sodium bicarbonate solution. The organic phases are dried, concentrated by evaporation and the residue is flash-chromatographed over 80 g of silica gel (grain size 0.04–0.063 mm) [eluant: methylene chloride/ether (4:1), fractions of approximately 25 ml]. Fractions 24–40 are combined, concentrated by evaporation, the residue is dissolved in a small amount of methylene chloride, and the solution is filtered and concentrated by evaporation once more. After drying the residue in a high vacuum, Z-Sta-Ala-OC(CH$_3$)$_3$ is obtained as a slightly yellowish oil; R$_f$ (methylene chloride/diethyl ether [4:1])=0.10.

Stage 13.2: 470 mg of Z-Sta-Ala-OC(CH$_3$)$_3$ (from stage 13.1) are dissolved in 10 ml of trifluoroacetic acid and the solution is stirred for 10 minutes at 25° C. The solvent is then removed in a rotary evaporator and the residue is flash-chromatographed over 200 g of silica gel (eluant first chloroform/methanol/concentrated aqueous ammonia solution [40:10:1], then chloroform/methanol/concentrated aqueous ammonia solution [5:3:1]). The product-containing fractions are combined and concentrated by evaporation, the residue is taken up in chloroform and the chloroform solution is extracted with dilute hydrochloric acid and saturated sodium chloride solution, dried and concentrated by evaporation. After drying the residue in a high vacuum, Z-Sta-Ala-OH is obtained in the form of a colourless foam; R$_f$ (G)=0.43.

Stage 13.3: 250 mg of Z-Sta-OH(cf. stage 1.12) are dissolved in 4 ml of 90% strength methanol. 1 ml of a 20% aqueous cesium carbonate solution is added to the solution, and the solvent is then removed in a rotary evaporator. The residue is twice dissolved in 2.5 ml of DMF and each time the DMF is removed again in a rotary evaporator. The residue is dried in a high vacuum, then dissolved in 2.5 ml of DMF and 55 μl of methyl iodide are added to the solution. The whole is stirred for 18 hours at 25° C., the solvent is then removed and the residue is taken up in ethyl acetate. After extraction twice with sodium chloride solution, the organic phase is dried over sodium sulphate and concentrated by evaporation. The residue is flash-chromatographed over 55 g of silica gel (eluant: chloroform/methanol [95:5]). The product-containing fractions are combined and concentrated by evaporation, yielding Z-Sta-OMe in the form of a yellowish oil; R$_f$ (chloroform/methanol [95:5])=0.49.

Stage 13.4: 818 mg of Z-Sta-OMe dissolved in 40 ml of methanol are hydrogenated at room temperature and normal pressure in the presence of 190 mg of palladium-on-carbon catalyst (10% Pd) until saturation. During hydrogenation, the pH value is maintained constantly at 5 by the continuous addition of 0.5N HCl. After hydrogenation the catalyst is filtered off and the filtrate is concentrated by evaporation. H-Sta-OMe×HCl is obtained in the form of a colourless foam; R$_f$(G)=0.21. This crude product is used directly in stage 13.5.

Stage 13.5: In a manner analogous to that described in stage 13.1, using as starting materials 150 mg of H-Sta-OMe×HCl (from stage 13.4), 253 mg of Z-Sta-Ala-OH (from stage 13.2), 102 mg of HOBt×H$_2$O, 67 mg of N-methylmorpholine and 178 mg of DCCI, Z-Sta-Ala-Sta-OMe is obtained; R$_f$ (chloroform/methanol ]9:1])=0.37.

Stage 13.6: 259 mg of Z-Sta-Ala-Sta-OMe (from stage 13.5) dissolved in 10 ml of 90% strength methanol are hydrogenated in the presence of 30 mg of palladium-on-carbon catalyst (10% Pd) at 25° under normal pressure with CO$_2$-absorption (CO$_2$ from the removal of the Z-protecting group) until saturation. The catalyst is filtered off, the filtrate is concentrated by evaporation and the residue is dried in a high vacuum. H-Sta-Ala-Sta-OMe is obtained in the form of a colourless foam; R$_f$(chloroform/methanol/ammonia [40:10:1])=0.41; R$_f$ (C)=0.29.

The starting material Z-Pro-Phe-His-OH can be obtained in the following manner:

Stage 13.7: 35 ml of water and 5.0 ml of 1N sodium hydroxide solution are added to 1.92 g of Z-Pro-Phe-His-OMe (H. Derwald et al., J. Med. Chem. 7, 50 [1964]) dissolved in 50 ml of methanol. The solution is stirred for 45 minutes at 25° and then neutralised with 5.0 ml of 1N hydrochloric acid. The solvent is removed and the residue is flash-chromatographed over 10 g of silica gel (eluant: chloroform/methanol/concentrated aqueous ammonia solution [5:3:1]; fractions of approximately 15 ml). Fractions 6–13 are combined, concentrated by evaporation and the residue is dissolved in 70 ml of water. After neutralisation to a pH value of 5.0 by the addition of dilute hydrochloric acid, extraction is carried out twice with n-butanol and the combined butanol phases are washed with water and concentrated by evaporation. After drying the residue in a high vacuum, Z-Pro-Phe-His-OH is obtained in the form of a colourless powder; $R_f(I)=0.23$.

EXAMPLE 14

125 mg of Z-Pro-Phe-His-Sta-Ala-Sta-OMe (from Example 13), dissolved in 10 ml of 90% strength methanol, are hydrogenated in the presence of 30 mg of palladium-on-carbon catalyst (10% Pd) at 25° under normal pressure with $CO_2$-absorption ($CO_2$ from the removal of the Z-protecting group) until saturation. The catalyst is then filtered off, the filtrate is concentrated by evaporation and the residue is dried in a high vacuum. H-Pro-Phe-His-Sta-Ala-Sta-OMe (cf. Example 9) is obtained in the form of a colourless foam; $R_f(G)=0.12$.

EXAMPLE 15

40 mg of H-Pro-Phe-His-Sta-Ala-Sta-OMe are dissolved in 10 ml of saturated methanolic ammonia solution. The solution is left to stand for 48 hours at room temperature, then the solvent is removed in a rotary evaporator and the residue is chromatographed over silica gel in the system chloroform/methanol/concentrated aqueous ammonia solution (40:10:1). The main fractions are combined and concentrated by evaporation. After drying the residue in a high vacuum, H-Pro-Phe-His-Sta-Ala-Sta-$NH_2$ (cf. Example 9) is obtained in the form of a colourless powder; $R_f$(chloroform/methanol/concentrated ammonia solution [40:10:1])=0.27.

EXAMPLE 16

677 mg of Z-Arg-Arg-Pro-Phe-His-OH×3HCl (see stage 4.4) (containing 24% by weight of NaCl), 272 mg of H-Sta-Sar-His-Lys(Boc)-OMe, 85 mg of HOBt×$H_2O$ and 48 μl of N-methylmorpholine are dissolved in 6 ml of DMF. After cooling to 0°, 124 mg of DCCI are added, and the whole is stirred for a few minutes then left to stand overnight at 0° and for 30 hours at room temperature. The DCH which has separated out is filtered off, the filtrate is concentrated to dryness, the residue is heated for 1 hour at 60° in 12 ml of methanol/glacial acetic acid/$H_2O$ (94:3:3), the solution is concentrated to approximately 3 ml and the crude product is precipitated by the addition of 30 ml of diisopropyl ether. In order to be converted into the acetate, the crude product is dissolved in 5 ml of 0.05N acetic acid, the small amount of insoluble material is filtered off and the filtrate is filtered slowly through a column of weakly basic anion exchanger (Merck No. II; length=11·cm, $\phi=1.2$ cm). The eluate is lyophilised and purified by means of Craig partitioning in the system n-butanol/glacial acetic acid/$H_2O$ (4:1:5) over 510 stages (K=0.4). The chromatographically uniform fractions are combined, concentrated to a small volume and lyophilised. Z-Arg-Arg-Pro-Phe-His-Sta-Sar-His-Lys(Boc)-OMe is thus obtained in the acetate form as an amorphous, readily water-soluble powder; $R_f$(D)=0.31; $R_f$(M)=0.44; $R_f$(O)=0.32.

The H-Sta-Sar-His-Lys(Boc)-OMe used as starting material can be obtained in the following manner:

Stage 16.1: 500 mg of Z-His-Lys(Boc)-OMe are dissolved in 10 ml of MeOH and 0.94 ml of 1N HCl. After the addition of 50 mg of Pd-on-carbon (10% Pd), hydrogenation with $CO_2$-absorption is carried out until saturation, then the catalyst is filtered off and the filtrate is concentrated to approximately 2 ml. 10 ml of DMF are added and the whole is again concentrated to 5 ml. This solution contains 401 mg of HCl×H-His-Lys(Boc)-OMe. 252 mg of Z-Sar-OH, 53 μl of N-methylmorpholine, 144 mg of HOBt×$H_2O$ and 252 mg of DCCI are added, stirring is briefly carried out until all components are dissolved, and then the whole is left to stand at room temperature for 20 hours. The DCH which has crystallised out is filtered off at 0°, the filtrate is concentrated to honey in a high vacuum, heated for one hour at 60° in 11 ml of methanol/glacial acetic acid/$H_2O$ (94:3:3) and again concentrated to 5 ml Precipitation is effected by the addition of 50 ml of diisopropyl ether, the whole is left to stand for 1 hour in an ice bath and the supernatant mother liquor is decanted. The crude product is purified by chromatography over 25 g of silica gel (Merck No. 60, 230–400 mesh) by elution with chloroform/methanol/$H_2O$/glacial acetic acid (180:20:2:1). In order to remove the acetic acid the pure fractions are dissolved in ethyl acetate, washed in succession with 5% aqueous sodium bicarbonate solution and $H_2O$ and, by concentration of the ethyl acetate phase, Z-Sar-His-Lys(Boc)-OMe is obtained in the form of an amorphous powder; $R_f(I)=0.45$; $R_f(G)=0.6$.

Stage 16.2: 390 mg of Z-Sar-His-Lys(Boc)-OMe are dissolved in 10 ml of 95% strength MeOH and, after the addition of 40 mg of Pd-on-carbon, hydrogenated with $CO_2$-absorption until saturation. The catalyst is filtered off, the filtrate is concentrated to dryness and the amorphous residue is dried to constant weight in a high vacuum at 40°, yielding H-Sar-His-Lys(Boc)-OMe; $R_f(G)=0.1$; $R_f(E)=0.25$.

Stage 16.3: 254 mg of Z-Sta-OH (see stage 1.12), 297 mg of H-Sar-His-Lys(Boc)-OMe, 97 mg of HOBt×$H_2O$ and 196 mg of DCCI are dissolved, in this sequence, in 3 ml of DMF and the whole is left to stand for 20 hours at room temperature. The DCH which has crystallised out is filtered off, the filtrate is concentrated to dryness, heated for 1 hour at 60° in 7 ml of methanol/glacial acetic acid/$H_2O$ (94:3:3), and this solution is again concentrated to dryness. The oily residue is purified by chromatography over 75 g of silica gel (Merck No. 60, 230–400 mesh) by elution with $CHCl_3$/MeOH (9:1). The pure fractions are dissolved in ethyl acetate, washed with $NaHCO_3$ solution and with $H_2O$ and, by concentration of the organic phase, Z-Sta-Sar-His-Lys(Boc)-OMe is obtained in amorphous form (honey); $R_f(F)=0.15$; $R_f(I)=0.5$.

Stage 16.4: 380 mg of Z-Sta-Sar-His-Lys(Boc)-OMe in 10 ml of 95% strength MeOH are hydrogenated with $CO_2$-absorption until saturation after the addition of 100 mg of Pd-on-carbon (10% Pd), the solution is filtered and concentrated to dryness. After drying in a high vacuum, H-Sta-Sar-His-Lys(Boc)-OMe is obtained in the form of an amorphous powder; $R_f(G)=0.18$; $R_f(E)=0.53$.

EXAMPLE 17

100 mg of Z-Arg-Arg-Pro-Phe-His-Sta-Sar-His-Lys(-Boc)-OMe (see Example 16) are dissolved in 2 ml of 95% strength MeOH and, after the addition of 10 mg of Pd-on-carbon (10% Pd), hydrogenated by passing hydrogen through until the starting material has disappeared completely (monitoring by thin layer chromatography). The catalyst is filtered off, the filtrate is concentrated to dryness and the residue is dissolved in 2 ml of $H_2O$ and lyophilised, yielding H-Arg-Arg-Pro-Phe-His-Sta-Sar-His-Lys(Boc)-OMe; $R_f$ (D)=0.15; $R_f$ (M)=0.25; $R_f$(O)=0.22.

EXAMPLE 18

77 mg of H-Arg-Arg-Pro-Phe-His-Sta-Sar-His-Lys(-Boc)-OMe (from Example 17) are dissolved in 0.4 ml of 95% strength TFA and left to stand for 25 minutes. By adding 5 ml of diisopropyl ether and filtering off the precipitate, H-Arg-Arg-Pro-Phe-His-Sta-Sar-His-Lys-OMe is obtained in the form of an amorphous, hygroscopic powder; $R_f$ (D)=0.04; $R_f$ (M)=0.04; $R_f$ (O)=0.05.

To produce the acetate, the resulting compound is as usual filtered through a column containing weakly basic ion exchanger in the acetate form.

EXAMPLE 19

110 mg of H-Arg-Arg-Pro-Phe-His-Sta-Sar-His-Lys-OMe (in the form of the trifluoroacetate; see Example 18) are dissolved in 1 ml of $H_2O$ and the pH value is adjusted to 5.0 with 0.5N $NH_3$. After the addition of 20 $\mu l$ of a 1% aqueous trypsin solution, the pH value is maintained at 5.0 by means of a pH stat while stirring at room temperature and adding 0.1N $NH_3$. After approximately 10-15 minutes the absorption of the base is complete. The solution is acidified with 200 $\mu l$ of glacial acetic acid, heated for 2 minutes in a boiling water bath, and lyophilised. In order to be converted into the acetate, the residue is dissolved in $H_2O$ and filtered slowly through a column ($\phi$=0.7 cm; length=8 cm) of weakly basic ion exchanger (for example Merck No. II) equilibrated in 0.05N acetic acid. The eluate is concentrated to a small volume and lyophilised, yielding H-Arg-Arg-Pro-Phe-His-Sta-Sar-His-Lys-OH (in acetate form) as an amorphous, readily water-soluble powder; $R_f$ (D)=0.03; $R_f$(M)=0.03; $R_f$(O)=0.03.

EXAMPLE 20

721 mg of Z-Arg-Arg-Pro-Phe-His-OH×3 HCl (see stage 4.4) (containing 24% by weight of NaCl), 176 mg of H-Sta-$\beta$-Ala-His-$NH_2$, 91 mg of HOBt×$H_2O$ and 50 $\mu l$ of N-methylmorpholine are dissolved in 5 ml of DMF. After cooling to 0°, 132 mg of DCCI are added and then the whole is stirred for 6 hours at 0° and left to stand overnight at room temperature. The DCH which has crystallised out is filtered off, the filtrate is concentrated to dryness and the residue is heated for 1 hour at 60° in 14 ml of methanol/glacial acetic acid/$H_2O$ (94:3:3). The solution is concentrated to 3 ml and the crude product is precipitated by the addition of 30 ml of diisopropyl ether. In order to convert it into the acetate, the product is dissolved in 5 ml of 0.05N acetic acid, a small amount of insoluble material is filtered off and the solution is filtered slowly through a column ($\phi$=1.2 cm, length=10 cm) of weakly basic ion exchanger in the acetate form (Merck II) equilibrated in 0.05N acetic acid. The eluate is concentrated to approximately 3 ml and lyophilised. Purification is effected by means of Craig partitioning over 750 stages in the system n-pentanol/glacial acetic acid/$H_2O$ (4:1:5); K=0.13. The chromatographically pure fractions are combined, concentrated to dryness and the residue is dissolved in 3 ml of $H_2O$ and lyophilised. Z-Arg-Arg-Pro-Phe-His-Sta-$\beta$-Ala-His-$NH_2$ (acetate form) is obtained in the form of an amorphous, water-soluble powder; $R_f$(D)=0.17; $R_f$ (M)=0.30; $R_f$(O)=0.25.

The H-Sta-$\beta$-Ala-His-$NH_2$ used as starting material can be obtained in the following manner:

Stage 20.1: 6.0 g of $\beta$-alanine are taken up in 33.7 ml of 2N NaOH and cooled to +5°. At this temperature there are then added dropwise, simultaneously, 22.5 ml of a 50% solution of chloroformic acid benzyl ester in toluene and 16.8 ml of 4N NaOH. The emulsion is subsequently stirred in an ice bath for 3 hours. After separating off the organic phase, the aqueous phase is extracted once more with ether and then, while cooling with an ice bath, the pH is adjusted to 1 with 44 ml of 2N HCl. By filterirg off the precipitate and drying in a high vacuum at 50°, Z-$\beta$-Ala-OH is obtained in the form of a white powder; $R_f$ ($CH_2Cl_2$/MeOH/concentrated aqueous ammonia solution [5:3:1])=0.37.

Stage 20.2: A solution of 12.3 g of Z-$\beta$-Ala-OH and 16.0 g of H-His-$OCH_3$×2 HCl in 300 ml of DMF is cooled to 0° and there are added dropwise thereto first a solution of 22.75 g of phosphoric acid diphenyl ester azide in 110 ml of DMF and then a solution of 30.7 ml of triethylamine in 110 ml of DMF. The suspension so obtained is stirred for 2 days at room temperature and then concentrated to an oily suspension in a high vacuum. The residue is taken up in ethyl acetate, washed with sodium bicarbonate and brine, dried and concentrated by evaporation. The crude product is separated by flash chromatography (1.6 kg of silica gel [type 60, Merck], 40-63 $\mu m$, 0.4 bar, fractions of 400 ml, eluant: $CH_2Cl_2$/MeOH[13:2]). By concentration by evaporation of the appropriate fractions, Z-$\beta$-Ala-His-$OCH_3$ is obtained as a slightly yellowish foam; $R_f$(L)=0.69.

Stage 20.3: 9.5 g of Z-$\beta$-Ala-His-$OCH_3$ are stirred overnight at room temperature in 95 ml of 7N methanolic ammonia solution. The suspension is diluted with 30 ml of methanol and stirred for a further 2.5 hours at room temperature. The crystals are filtered off and dried at 30° in a high vacuum. The mother liquor is concentrated by evaporation and the residue is dissolved in 80 ml of isopropanol. 200 ml of ether are added and the whole is left to crystallise out again while stirring at room temperature overnight. The filterod-off crystals are also dried. The crystals from both crystallisations consist of Z-$\beta$-Ala-His-$NH_2$ (slightly beige, m.p. 181°-182°); $R_f$(C)=0.57.

Stage 20.4: 8.19 g of Z-$\beta$-Ala-His-$NH_2$ are hydrogenated at room temperature under normal pressure for 15 hours in 200 ml of methanol/water (95:5) with 0.82 g of palladium-on-carbon (5% Pd). After filtering off the catalyst, evaporating off the solvent and drying, H-$\beta$-Ala-His-$NH_2$ is obtained in the form of a colourless powder; $R_f$(L)=0.01.

Stage 20.5: 370 mg of Z-Sta-OH, 225 mg of H-$\beta$-Ala-His-$NH_2$, 153 mg of HOBt×$H_2O$ and 247 mg of DCCI are suspended in 4.5 ml of DMF and stirred at room temperature. After approximately 10 minutes a clear solution has formed and afrer approximately 20 minutes DCH begins to crystallize out. The mixture is left to stand overnight, then stirred for 30 minutes at 0°, DCH is filtered off und the filtrate is concentrated to an oil.

This is heated for 1 hour at 60° in 14 ml of methanol/glacial acetic acid/$H_2O$ (94:3:3), the solution is concentrated to 3 ml and the crude product is precipitated by 30 ml of diisopropyl ether and dried. To remove the acetic acid, the residue is dissolved in n-butanol, washed in succession with 5% strength $NaHCO_3$ solution and with water, and the butanol phase is again concentrated to dryness. After purification by chromatography over 30 g of silica gel (Merck No. 60, 230–400 mesh) using as eluant chloroform/methanol (75:25), Z-Sta-β-Ala-His-$NH_3$ is obtained; $R_f(G)=0.28$.

Stage 20.6: 240 mg of Z-Sta-β-Ala-His-$NH_2$ are hydrogenated in 10 ml of 95% strength methanol with 50 mg of Pd-on-carbon (10% Pd) with $CO_2$-absorption until saturation. The catalyst is filtered off, the filtrate is concentrated to dryness and the solid amorphous residue is pulverised and then dried in a high vacuum, yielding H-Sta-β-Ala-His-$NH_2$; $R_f$ (E)=0.11; $R_f$ (M)=0.26.

EXAMPLE 21

98 mg of Z-Arg-Arg-Pro-Phe-His-Sta-β-Ala-His-$NH_2$ (from Example 20) are dissolved in 2 ml of 95% strength MeOH and hydrogenated with 20 mg of Pd-on-carbon (10% Pd), while stirring with a magnet and passing hydrogen through, until the starting material has disappeared. The catalyst is then filtered off, the filtrate is concentrated to dryness and the vitreous residue is dissolved in 2 ml of $H_2O$ and lyophilised, yielding H-Arg-Arg-Pro-Phe-His-Sta-β-Ala-His-$NH_2$ in the form of an amorphous powder; $R_f$ (D)=0.05; $R_f$ (M)=0.06; $R_f$(O)=0.06.

EXAMPLE 22

333 mg of Z-Arg-Arg-Pro-Phe-His-OH×3 HCl (see stage 4.4; containing 24% by weight of NaCl), 106 mg of H-Sta-Lac-His-$NH_2$×2 HCl, 36 mg of HOBt×$H_2O$ and 64 μl of N-methylmorpholine are dissolved in 1 ml of DMF. At 0°, 86 mg of DCCI are added, the whole is stirred for 10 minutes and is then left to stand for 15 hours at 0° and for 2 days at room temperature. The insoluble components (NaCl and DCH) are filtered off and washed with DMF, the filtrate is concentrated to an oil, heated at 60° for 1 hour in 10 ml of methanol/glacial acetic acid/$H_2O$ (94:3:3) and again concentrated. By triturating with 40 ml of diisopropyl ether, decanting and drying the residue, a crude product is obtained, which is dissolved in 4 ml of 0.05N acetic acid and converted into the acetate by filtering slowly through a column (φ=1 cm, length=10 cm) of weakly basic ion exchanger (acetate form, Merck II). The eluate is concentrated to approximately 3 ml and lyophilised and the residue is purified by Craig partitioning over 920 stages in the system n-butanol/glacial acetic acid/$H_2O$ (4:1:5) (K=0.14). The pure fractions are combined, concentrated to dryness, the residue is dissolved in 2 ml of $H_2O$ and lyophilised. The so-obtained acetate of Z-Arg-Arg-Pro-Phe-His-Sta-Lac-His-$NH_2$ is amorphous and readily water-soluble; $R_f$ (D)=0.23; $R_f$ (M)=0.36; $R_f$ (O)=0.29.

The H-Sta-Lac-His-$NH_2$ used as starting material can be obtained in the following manner:

Stage 22.1: A solution of 138 mg of (3S,4S)-N-Boc-statin (for manufacture cf. for example. D. H. Rich et. al., J. Org. Chem. 43, 3624 [1978]), 90 mg of (L)-lactic acid benzyl ester and 62 mg of 4-dimethylaminopyridine, dissolved in 9 ml of absolute methylene chloride (filtered through aluminium oxide with the activity stage I), has added to it, at 25°, a solution of 124 mg of DCCI in 3 ml of absolute methylene chloride. After a few minutes, DCH precipitates from the resulting solution. After 2 hours, filtration is carried out and the filtrate is concentrated by evaporation to a small volume. The solution remaining is flashchromatographed over 90 g of silica gel (grain size 0.04–0.063 mm) at a pressure of approximately 0.3 bar (eluant: $CH_2Cl_2$/diethyl ether [4:1], fractions of approximately 20 ml). Fractions 6 and 7 are combined and the solvent is removed in a rotary evaporator. Boc-Sta-Lac-$OCH_2$-$C_6H_5$ is obtained in the form of a yellowish oil, which is used directly in stage 22.2; $R_f$($CH_2Cl_2$/diethyl ether [4:1])=0.44.

Stage 22.2: A solution of 79 mg of Boc-Sta-Lac-$OCH_2$-$C_6H_5$ in 10 ml of absolute dioxan is hydrogenated at 25° for 4 hours in the presence of 20 mg of palladium-on-carbon catalyst (10% Pd). The catalyst is filtered off, the filtrate is concentrated by evaporation and the residue is dried in a high vacuum. Boc-Sta-Lac-OH is obtained in the form of a colourless oil, which is used directly in stage 22.3; $R_f(G)=0.60$.

Stage 22.3: 63 mg of Boc-Sta-Lac-OH, 28 mg of H-His-$NH_2$ and 28 mg of HOBt×$H_2O$ are dissolved in 2 ml of DMF. The solution is cooled in an ice bath and 49 mg of DCCI are added. The whole is stirred for 4 hours at 0° and for 16 hours at 25°, DCH being precipitated. The suspension is filtered, the filtrate is concentrated by evaporation in a high vacuum and the residue is taken up in 3 ml of a methanol/glacial acetic acid/water mixture (94:3:3) and stirred for 1 hour at 60°. The suspension is again concentrated by evaporation, the residue is suspended in a small amount of methanol/ethyl acetate (1:1), filtered and the filtrate is concentrated to dryness. The residue is flash-chromatographed over 35 g of silica gel at approximately 0.3 bar (eluant: methylene chloride/methanol/concentrated aqueous ammonia solution [80:10:1], fractions of approximately 10 ml). Fractions 24–35 are combined, the solvent is removed, the residue is taken up in a small amount of methanol, the solution is filtered and the filtrate is again concentrated by evaporation. After drying the residue in a high vacuum, Boc-Sta-Lac-His-$NH_2$ is obtained in the form of a colourless powder, which is used directly in stage 22.4; $R_f$ ($CH_2Cl_2$/MeOH/concentrated aqueous ammonia solution [40:10:1])=0.62.

Stage 22.4: 118 mg of Boc-Sta Lac-His-$NH_2$ are dissolved in 1.18 ml of methanol, 2.36 ml of 5N HCl in dioxan are added, and the whole is left to stand for 2 minutes. An oil is precipitated by the addition of 30 ml of diisopropyl ether/petroleum ether (1:1), the whole is left to stand for 20 minutes at 0°, the supernatant mother liquor is decanted and the oil is dried in a high vacuum. The residue is dissolved in 4 ml of $H_2O$ and lyophilised, yielding H-Sta-Lac-His-$NH_2$ (as the hydrochloride) in the form of an amorphous, hygroscopic powder; $R_f$ (B)=0.05; $R_f$(M)=038; $R_f$(O)=0.26.

EXAMPLE 23

30 mg of Z-Arg-Arg-Pro-Phe-His-Sta-Lac-His-$NH_2$ (see Example 22) are dissolved in 1 ml of 95% strength methanol and, after the addition of 10 mg of Pd-on-carbon (10% Pd), hydrogenated while stirring and passing hydrogen through. When the reaction is complete (monitoring by thin layer chromatography), the catalyst is filtered off, the filtrate is concentrated to dryness, and the residue is dissolved in 0.6 ml of $H_2O$ and lyophilised, yielding H-Arg-Arg-Pro-Phe-His-Sta-Lac-His-$NH_2$ as an acetate in the form of an amorphous water-soluble powder; $R_f(D)=0.07$; $R_f(M)=0.09$; $R_f(O)=0.09$.

EXAMPLE 24

The compounds listed below are obtained in accordance with the procedures described in this application:

Z-Arg-Arg-Pro-Phe-His-Sta(Ac)-Ile-His-Lys(Boc)-OCH₃,

H-Pro-His-Pro-Phe-His-Sta-Phe-Ile-His-Lys-OH; with $R_f(M)=0.14$ and $R_f(N)=0.14$, H-Arg-D-Arg-Pro-Phe-His-Sta-Ile-His-Lys-OH (cf. Example 3); with $R_f(M)=0.06$, $R_f(N)=0.08$ and $R_f(D)=0.12$, H-Pro-His-Pro-Phe-D-His-Sta-Phe-Ile-His-Lys-OH, with $R_f(M)=0.15$, $R_f(K)=0.23$ and $R_f(D)=0.17$, H-Pro-His-Pro-Phe-His-(3R,4S)-Sta-Ile-His-Lys-OH, with $R_f(M)=0.125$, $R_f(K)=0.14$ and $R_f(D)=0.125$, H-Pro-His-Pro-Phe-D-His-Sta-Ile-His-Lys-OH, with $R_f(M)=0.10$, $R_f(K)=0.21$ and $R_f(D)=0.125$, Z-Ile-His-Pro-Phe-His-Sta-Ile-His-Lys(Boc)-OMe, with $R_f(B)=0.30$ and $R_f(E)=0.71$, H-Ile-His-Pro-Phe-His-Sta-Ile-His-Lys-OH, with $R_f(M)=0.21$, $R_f(N)=0.14$ and $R_f(D)=0.20$, Z-Arg-His-Pro-Phe-His-Sta-Ile-His-Lys(Boc)-OMe, with $R_f(B)=0.58$, $R_f(M)=0.52$ and $R_f(E)=0.19$, H-Arg-His-Pro-Phe-His-Sta-Ile-His-Lys-OH, with $R_f(M)=0.04$, $R_f(N)=0.13$ and $R_f(D)=0.08$.

We claim:

1. Compounds of the formula

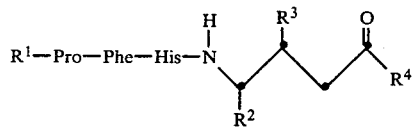

wherein R¹ represents the radical H-Pro-His-, H-Ile-His- or H-Arg-Arg-, R² represents 2-methylpropyl, R³ represents hydroxy, R⁴ represents the radical -Val-Tyr-Lys-OH, -Ile-His-Lys-OH, -Ile-His-Ser-OH, -Val-Tyr-Ser-OH, -Val-Tyr-OH, -Ile-His-OH, -Val-Tyr-NH₂, -Ile-His-NH₂ or -Ala-Sta-OH, or such radical wherein the amino acid residue -Ile- is replaced by -β-Ala- or the residue -Val-, -Ile- or -Ala- replaced by -Lac- or -OCH₂CO-, and a compound wherein the carboxy and amino groups in R¹ and R⁴ are protected by pharmaceutically acceptable protecting groups, and pharmaceutically acceptable salts of these compounds.

2. Compounds of claim 1 in which R¹ represents the radical H-Pro-His-, R² represents 2-methylpropyl, R³ represents free hydroxy, and R⁴ represents the radical -Val-Tyr-Lys-OH, -Ile-His-Lys-OH, -Ile-His-Ser-OH, -Val-Tyr-Ser-OH, -Val-Tyr-OH, -Ile-His-OH, -Val-Tyr-NH₂, -Ile-His-NH₂ or -Ala-Sta-OH, and pharmaceutically acceptable salts of these compounds.

3. Compounds of claim 1 in which R¹ represents the radical H-Ile-His-, R² represents 2-methylpropyl, R³ represents free hydroxy, and r⁴ represents the radical -Val-Tyr-Lys-OH, -Ile-His-Lys-OH, -Ile-His-Ser-OH, -Val-Tyr-Ser-OH, -Val-Tyr-OH, -Ile-His-OH, -Val-Tyr-NH₂, -Ile-His-NH₂ or -Ala-Sta-OH, and pharmaceutically acceptable salts of these compounds.

4. Compounds of claim 1 wherein -β-Ala- replaces the amino acid residue -Ile- in the radical R⁴ and salts of such compounds having salt-forming groups.

5. Compounds of claim 1, wherein -Lac-replaces the amino acid residue -Val-, -Ile- or -Ala- in the radical R⁴ and salts of such compounds having salt-forming groups.

6. Compounds of claim 1, wherein —OCH₂CO— replaces the amino acid residue -Val-, -Ile- or -Ala- in the radical R⁴ and salts of such compounds having salt-forming groups.

7. Compounds of claim 1 in which all free amino groups are in protected form, and salts of such compounds having salt forming groups.

8. Compounds of claim 1 in which free carboxy groups are in protected form, and salts of such compounds having salt-forming groups.

9. The compound H-Pro-His-Pro-Phe-His-Sta-Val-Tyr-Lys-OH or H-Pro-His-Pro-Phe-His-Sta-Ile-His-Lys-OH and its pharmaceutically acceptable salts according to claim 1.

10. The compound benzyloxycarbony-Arg-Arg-Pro-Phe-His-Sta-Ile-His-Lys(tert.-butoxycarbonyl)-OMe and its pharmaceutically acceptable salts according to claim 1.

11. A compound selected from the group consisting of benxyloxycarbonyl-Arg-Arg-Pro-Phe-His-Sta-Ile-His-Lys-OMe, H-Arg-Arg-Pro-Phe-His-Sta-Ile-His-Lys-OMe and H-Arg-Arg-Pro-Phe-His-Sta-Ile-His-Lys-OH, and its pharmaceutically acceptable salts according to claim 1.

12. The compound H-Arg-Arg-Pro-Phe-His-Sta-Ile-His-Lys(tert.-butoxycarbonyl)-OMe and its pharmaceutically acceptable salts according to claim 1.

13. A compound selected from the group consisting of benzyloxycarbonyl-Arg-Arg-Pro-Phe-His-Sta-β-Ala-His-NH₂ and and H-Arg-Arg-Pro-Phe-His-Sta-β-Ala-His-NH₂, and its pharmaceutically acceptable salts according to claim 1.

14. A compound selected from the group consisting of benzyloxycarbonyl-Arg-Arg-Pro-Phe-His-Sta-Lac-His-NH₂ and H-Arg-Arg-Pro-Phe-His-Sta-Lac-His-NH₂, and its pharmaceutically acceptable salts according to claim 1.

15. A pharmaceutical preparation for treating reninassociated hyperaldosteronism that contains an effective amount of a compound according to claim 1 together with a signficant amount of pharmaceutical carrier.

16. Method of treating a warm-blooded animal including man suffering from renin-associated hyperaldosteronism, comprising administering to said animal a therapeutically effective amount of a compound according to claim 1.

17. Compounds of claim 1 in which the carboxy groups thereof are protected in the form of lower alkyl esters and amino groups are protected in the form of a tert.-butoxycarbonylamino or a benzyloxycarbonylamino group.

* * * * *